US010835485B2

(12) United States Patent
Pompejus

(10) Patent No.: US 10,835,485 B2
(45) Date of Patent: Nov. 17, 2020

(54) ORAL HEALTH IMPROVING COMPOSITIONS

(71) Applicant: BASF SE, Ludwigshafen (DE)

(72) Inventor: Markus Pompejus, White Plains, NY (US)

(73) Assignee: BASF SE (DE)

( * ) Notice: Subject to any disclaimer, the term of this patent is extended or adjusted under 35 U.S.C. 154(b) by 0 days.

(21) Appl. No.: 15/370,500

(22) Filed: Dec. 6, 2016

(65) Prior Publication Data

US 2017/0273895 A1 Sep. 28, 2017

Related U.S. Application Data

(63) Continuation of application No. 13/981,194, filed as application No. PCT/EP2012/050463 on Jan. 12, 2012, now abandoned.

(60) Provisional application No. 61/435,472, filed on Jan. 24, 2011.

(30) Foreign Application Priority Data

Jan. 24, 2011 (EP) .................................... 11151924

(51) Int. Cl.
| A61K 8/99 | (2017.01) |
| A23L 33/135 | (2016.01) |
| A61K 35/74 | (2015.01) |
| A23K 10/16 | (2016.01) |
| A23K 10/18 | (2016.01) |
| A23K 50/42 | (2016.01) |
| A61Q 11/00 | (2006.01) |
| A61P 1/02 | (2006.01) |

(52) U.S. Cl.
CPC ................ *A61K 8/99* (2013.01); *A23K 10/16* (2016.05); *A23K 10/18* (2016.05); *A23K 50/42* (2016.05); *A23L 33/135* (2016.08); *A61K 35/74* (2013.01); *A61P 1/02* (2018.01); *A61Q 11/00* (2013.01)

(58) Field of Classification Search
None
See application file for complete search history.

(56) References Cited

U.S. PATENT DOCUMENTS

| 8,192,978 | B2* | 6/2012 | Kaesler .................. A23G 3/366 |
| | | | 435/252.9 |
| 8,506,953 | B2* | 8/2013 | Bottner .................... A61K 8/99 |
| | | | 424/93.45 |
| 8,921,060 | B2 | 12/2014 | Cooper |
| 2004/0101495 | A1 | 5/2004 | Nase et al. |
| 2006/0106129 | A1 | 5/2006 | Gernon et al. |
| 2008/0118444 | A1 | 5/2008 | Hsu et al. |
| 2008/0193427 | A1* | 8/2008 | Kaesler ................... A23G 3/366 |
| | | | 424/93.45 |
| 2010/0047190 | A1 | 2/2010 | Reindl et al. |
| 2012/0128645 | A1 | 5/2012 | Nikawa |
| 2012/0230923 | A1 | 9/2012 | Cooper |
| 2020/0085727 | A1* | 3/2020 | Kaesler .................... A61K 8/99 |

FOREIGN PATENT DOCUMENTS

| CN | 101948773 A | 1/2011 |
| DE | 202009011379 U1 | 12/2010 |
| EP | 1362897 A2 | 11/2003 |
| JP | 2008512104 A | 4/2008 |
| RU | 2352345 C1 | 4/2009 |
| WO | WO-9932563 A2 | 7/1999 |
| WO | WO-2006/027265 A1 | 3/2006 |
| WO | WO-2008/074473 A2 | 6/2008 |
| WO | WO-2011/007584 A1 | 1/2011 |
| WO | WO-2011057872 A1 | 5/2011 |

OTHER PUBLICATIONS

International Search Report for International Application No. PCT/EP2012/050463, dated Mar. 19, 2012.
International Preliminary Report On Patentability for International Application No. PCT/EP2012/050463, dated Jul. 30, 2013.
"New microorganisms chosen from *Lactobacillus rhamnosus, Lactobacillus casei* and *Lactobacillus paracasei* are useful in composition for treating intraoral disease e.g. caries caused by microorganisms e.g. *Candida albicans*", Database WPI, Accession No. 2011-A97541, XP-002671048, dated Jul. 16, 2009.

* cited by examiner

*Primary Examiner* — Mary Maille Lyons
(74) *Attorney, Agent, or Firm* — Faegre Drinker Biddle & Reath LLP

(57) ABSTRACT

The present invention is concerned with microorganisms or fragments thereof as sensorically neutral oral care agents, particularly for prevention of dental calculus, as anti-caries agents and/or anti-oral malodor agents. The invention is furthermore concerned with compositions comprising microorganisms or fragments thereof for reducing *mutans Streptococci*. Such compositions can be used in oral care compositions, e.g. for caries prophylaxis, or for prophylaxis of dental calculus or oral malodor. They may also or instead be used for prevention or treatment of oral malodor. As the microorganisms and fragments thereof according to the present invention have a very low, unobtrusive smell and taste, they are particularly suited as sensorically neutral agents for preventment of dental calculus, caries, oral biofilm formation and/or for prevention or treatment of oral malodor. The microorganisms and fragments thereof, and also compositions comprising such microorganisms and fragments, can thus advantageously be used in food and feed compositions, particularly in pet foods. Furthermore, the invention is concerned with methods of preparing such microorganisms, fragments, compositions, foods and feeds.

6 Claims, 3 Drawing Sheets

ORAL HEALTH IMPROVING COMPOSITIONS

RELATED APPLICATIONS

This application is a continuation of U.S. application Ser. No. 13/981,194, filed Jul. 23, 2013, which is incorporated by reference herein in its entirety, which is a national stage application (under 35 U.S.C. § 371) of PCT/EP2012/050463, filed Jan. 12, 2012, which claims benefit of U.S. Provisional Application No. 61/435,472, filed Jan. 24, 2011, and European Patent Application No. 11151924.5, filed Jan. 24, 2011.

The present invention is concerned with microorganisms or fragments thereof as sensorically neutral oral care agents, particularly for prevention of dental calculus, as anti-caries agents and/or anti-oral malodor agents. The invention is furthermore concerned with compositions comprising microorganisms or fragments thereof for reducing *mutans Streptococci*. Such compositions can be used in oral care compositions, e.g. for caries prophylaxis, or for prophylaxis of dental calculus or oral malodor. They may also or instead be used for prevention or treatment of oral malodor. As the microorganisms and fragments thereof according to the present invention have a very low, unobtrusive smell and taste, they are particularly suited as sensorically neutral agents for preventment of dental calculus, caries, oral biofilm formation and/or for prevention or treatment of oral malodor. The microorganisms and fragments thereof, and also compositions comprising such microorganisms and fragments, can thus advantageously be used in food and feed compositions, particularly in pet foods. Furthermore, the invention is concerned with methods of preparing such microorganisms, fragments, compositions, foods and feeds.

One of the notorious problems of tooth-bearing animals is the decay of such teeth. This problem is of particular importance to such animals that cannot, like sharks, shed their teeth to continuously replace them by a new set. Among the most important causes for tooth decay is caries. By the action of microorganisms colonizing the oral cavity dental enamel is continuously weakened and ultimately dissolved, leading to the formation of cariotic lesions. Such lesions in turn are suitable for further colonization of microorganisms, aggravating the problem of caries.

A problem unrelated to the formation of caries is the development of oral malodor. Oral malodor is considered the result of unwanted microorganisms colonizing the oral cavity. However, no single microorganism has so far been indicated as the primary cause for oral malodor. It seems to be clear, however, that the formation of caries and of oral malodor are independent processes, as oral malodor can also occur in the absence of teeth, and caries can occur in the absence of oral malodor.

Another problem of oral health particularly in animals is the formation of dental calculus. Calcified deposits on teeth are formed by microorganisms colonizing the surfaces of teeth. Typically, within 7-10 days calcified deposits on teeth have grown to such extent that they are visible to the naked eye. Dental calculus forms a focus to allow colonization of teeth by further microorganisms. This, in turn, can lead to the development of oral malodor, caries and inflammations of gingival tissue. There is thus a need for the prevention of the development of dental calculus, e.g. by slowing down dental calculus formation.

It has therefore frequently be tried to ameliorate these problems independently. Among the most notable solutions so far common in the art are tooth pastes and mouth washes. Such tooth pastes and mouth washes generally comprise antimicrobially effective agents to reduce the number of or inhibit the activity of tooth colonizing microorganisms, particularly caries causative microorganisms and/or oral malodor generating microorganisms. However, due to the uncorrelatedness of caries and oral malodor formation, many agents effective against caries are ineffective for prevention or treatment of oral malodor, and vice versa. Also, efficiency against dental calculus formation needs to be improved.

Another problem is that antimicrobially effective substances frequently exhibit a strong intrinsic smell or taste, which is considered repulsive by consumers and particularly by pet animals. Thus, compositions for oral care frequently comprise further olfactorily active agents to mask or alter the taste or smell inherent in the antimicrobially effective substances. However, such further agents are also not readily accepted by consumers due to their even stronger intrinsic taste or smell. This results in an undesirably low compliance of consumers to the application recommendations of manufacturers of such oral care compositions.

The problem of compliance is particularly important with children and animals. Both are prone to devising cunning ways of avoiding oral care compositions or of misusing them, e.g. by swallowing, such that an antimicrobially effective agent or agents cannot fully exert their intended action. Resistance particularly of pet animals like cats and dogs to any form of medication is frequently lamented. Also, such animals are known to avoid medications including antimicrobially effective oral care compositions even when hidden in a feed they would otherwise accept. In addition certain modes of applications for oral care compositions are not available for animals, as they for example are unable to gargle. Also, certain treatments of the oral cavity are particularly stressful to animals and would require anesthesia. For example, animals like cats and dogs will furiously resist removal of dental calculus.

In summary, oral hygiene is considered tedious for human beings including children and for animals including pet animals alike. The present invention therefore intends to ameliorate the above problems of prior art. In particular the present invention aims at increasing compliance with oral care instructions for human beings and for animals and particularly pet animals.

DETAILED DESCRIPTION OF THE INVENTION

Figure 1:
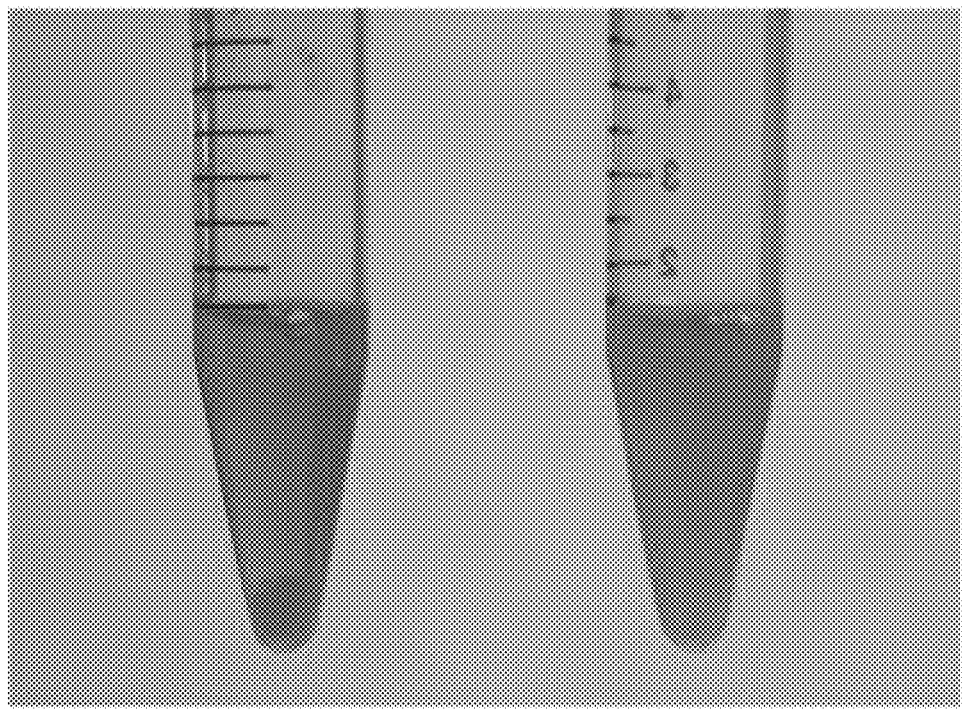
FIGS. 1 and 2 show an aggregation of *S. mutans* by *Lactobacillus*, as noted in Example 4 below.
Figure 2:
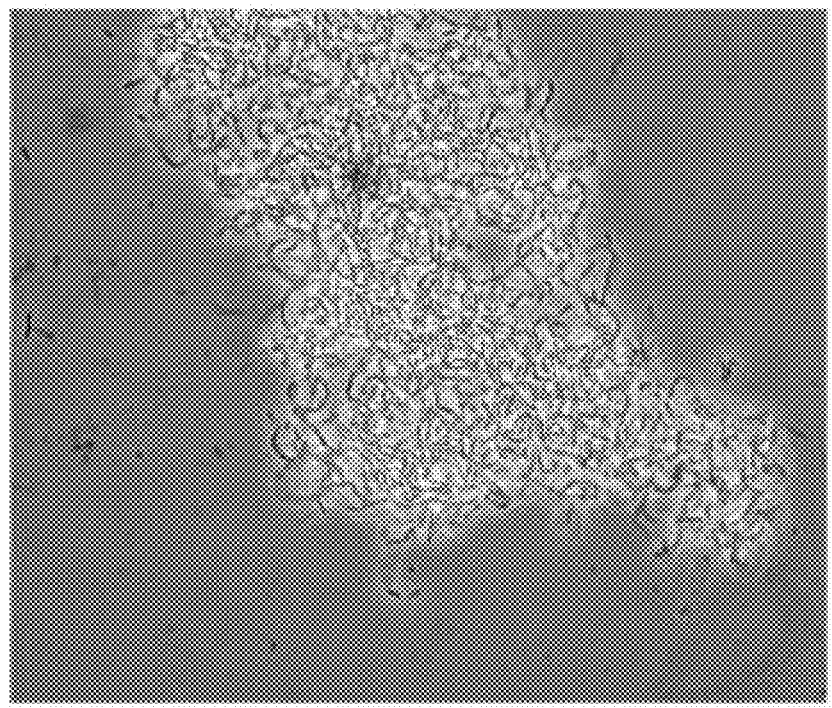

According to the invention, it is important for furthering compliance that the agent or agents used for prevention of dental calculus, caries and/or for prevention or treatment of oral malodor has a low intrinsic taste and scent. Thus, instead of masking or altering the taste and smell such agents by addition of further strongly tasting or smelling agents the present invention is concerned with a different approach. The inherent taste and smell of oral care agents had so far being overlooked or not been considered to be of major importance. Furthermore, it has now surprisingly turned out that agents are available which are both effective for prevention of dental calculus, caries and/or prevention or therapy of oral malodor without having a strong inherent taste or smell. It has also surprisingly been found that such agents are useful to increase compliance with oral care instructions and particularly to reduce oral care avoidance behavior in humans, including children, and animals, including pet animals. Also, the present invention allows to prepare oral care compositions having other flavors or fragrances than previously required for masking or altering the taste or smell of anti-calculus agents, anti-caries agents and/or anti-oral-malodor agents.

The present invention is concerned with microorganisms or fragments thereof as sensorically neutral oral care agents. The invention is furthermore concerned with compositions comprising microorganisms or fragments thereof for reducing *mutans Streptococci*. Such microorganisms and fragments thereof, and also such compositions, can be used for treatment or prevention of dental calculus. Such microorganisms, fragments or compositions can also be used in caries treatment or prophylaxis. They may also or instead be used for prevention or treatment of oral malodor. As the microorganisms and fragments thereof according to the present invention have a very low, unobtrusive smell and taste, they are particularly suited as sensorically neutral agents for preventment of caries, oral biofilm formation including formation of dental calculus and/or for prevention or treatment of oral malodor. The microorganisms and fragments thereof, and also compositions comprising then, can thus advantageously be used in food and feed compositions, particularly in pet foods. Furthermore, the invention is concerned with methods of preparing such microorganisms, fragments, compositions, foods and feeds.

According to the invention, the microorganism or fragment thereof useful as a sensorically neutral oral care agent, preferably is a lactic acid bacterium.

As indicated above, it has now surprisingly been found that lactic acid bacteria can be used as sensorically neutral oral care agents, particularly for prophylaxis and treatment of dental calculus, as anti-caries and/or anti-oral malodor agents. This could not be expected, as lactic acid bacteria are commonly known to exhibit a strongly sour or acidic flavor and/or smell, e.g. in yoghurt and other milk products.

According to the present invention, a lactic acid bacterium is any microorganism taxonomically of order Lactobacillales, and preferably is of family Lactobacillaceae. A microorganism according to the invention is considered to belong to a specified taxonomic group if it is more similar to a type strain within this taxonomic group or within a lesser taxonomic rank than to any type strain belonging to a taxonomic group other than the group in question or its lesser ranks, wherein said analysis is based on a comparison of their respective genetic material excluding plasmids and non-integrated viruses. Thus, a microorganism is considered to belong to the family of Lactobacillaceae if it is, as defined in the previous sentence, genetically more similar to a type strain of a species or genus within the family of Lactobacillaceae compared to type strains of a species or genus belonging to another family within the order of Lactobacillales.

Similarity according to the present invention is assessed using the Needleman-Wunsch global alignment algorithm. This algorithm is the standard algorithm to find the optimum alignment including gaps of two nucleic acid sequences along their entire length. The algorithm of Needleman and Wunsch has been published in 1970 J. Mol. Biol. 48, 443-453, wherein a penalty for a gap of n positions is computed according to the formula $$\text{gap opening penalty} + (n-1) \times \text{gap extension penalty.}$$

There is no penalty for hanging ends.

Gap open penalty in the context of the present invention is 10.0. The gap extension penalty in the context of the present invention is 0.5. The scoring matrix for comparing nucleic acid sequences in the context of the present invention is the unitary DNA identity matrix, which assigns a score of 1 for each identical base "substitution", and −10000 for all other base substitutions. Sequence alignments can be performed with these parameters e.g. via publicly available tools offered by the EBI.

A particular advantage inherent in microorganisms of the family of Lactobacillaceae is that they can generally be considered save for consumption by human beings and animals. For example, lactic acid bacteria have been used for a long time in the manufacture of foods for example by processing milk. They are also easy to handle due to their low danger to human or animal health and they are easy to cultivate in large quantities, e.g. in batches of 500 l of culture medium. Particularly preferred methods of cultivation will be described later.

Among the members of family of Lactobacillaceae, such lactic acid bacteria are particularly preferred according to the present invention which belong to genus *Lactobacillus, Paralactobacillus, Pediococcus* or *Sharpea*, wherein microorganisms of genus *Lactobacillus* are most preferred. Such microorganisms have been extensively used in the preparation of foods and feeds; they are easy to handle and can be produced in large quantities. Furthermore, within the family of Lactobacillaceae it is particularly among genus *Lactobacillus* that microorganisms can be obtained which are both sensorically neutral and effective as oral care agents, particularly as anti-dental calculus agents, anti-caries agents and/or anti-oral-malodor agents.

The lactic acid bacteria of the present invention are preferably rod-shaped or spherical, varying from long and slender to short bent rods, are moreover preferably immotile and/or asporogenous and produce lactic acid as a major or sole product of fermentative metabolism. The genus *Lactobacillus* to which the microorganism of the present invention belongs in a preferred embodiment is divided up by the following characteristics into three major subgroups, whereby it is envisaged that the *Lactobacillus* species of the present invention can belong to each of the three major subgroups:

(a) homofermentative lactobacilli
   (i) producing lactic acid, preferably the L-, D- or DL-isomer(s) of lactic acid in an amount of at least 85% from glucose via the Embden-Meyerhof pathway;
   (ii) growing at a temperature of 45° C., but not at a temperature of 15° C.;
   (iii) being long-rod shaped; and
   (iv) having glycerol teichoic acid in the cell wall;

(b) homofermentative lactobacilli
   (i) producing lactic acid, preferably the L- or DL-isomer(s) of lactic acid via the Embden-Meyerhof pathway;
   (ii) growing at a temperature of 15° C., showing variable growth at a temperature of 45° C.;
   (iii) being short-rod shaped or coryneform; and
   (iv) having ribitol and/or glycerol teichoic acid in the cell wall;

(c) heterofermentative lactobacilli
  (i) producing lactic acid, preferably the DL-isomer of lactic acid in an amount of at least 50% from glucose via the pentose-phosphate pathway;
  (ii) producing carbondioxide and ethanol
  (iii) showing variable growth at a temperature of 15° C. or 45° C.;
  (iv) being long or short rod shaped; and
  (v) having glycerol teichoic acid in the cell wall.

Based on the above-described characteristics, the microorganisms preferred according to the present invention can be classified to belong to the group of lactic acid bacteria, particularly to the genus of *Lactobacillus*.

In a preferred embodiment, the microorganism of the present invention has a metabolic fingerprint selected from the group consisting of:
(i) it metabolizes D-lactose, but not L-sorbose and/or D-saccharose and/or D-inuline,
(ii) it metabolizes inuline,
(iii) it metabolizes L-sorbose, but not D-lactose and/or D-saccharose and/or inuline, and
(iv) it metabolizes L-sorbose, D-lactose and inuline.

Preferably, the microorganism of the present invention has a metabolic fingerprint selected from the group consisting of:
(i) it metabolizes D-lactose, but not L-sorbose, D-saccharose and inuline,
(ii) it metabolizes L-sorbose, D-lactose and inuline, but not D-saccharose,
(iii) it metabolizes L-sorbose, but not D-lactose, D-saccharose and inuline, and
(iv) it metabolizes L-sorbose, D-lactose, D-saccharose, but not inuline.

Of course, the microorganism of the present invention is not limited to the metabolization of the aforementioned sugars of the metabolic fingerprint patterns, but may be capable of metabolizing further sugars.

Within the present invention, the term "microorganism" not only refers to such microorganisms which, when placed in the appropriate culturing conditions, can multiply (viable microorganisms). It is a particular advantage of the present invention that instead of such viable microorganisms also the corresponding thermally inactivated or lyophilized microorganisms can be used. This is particularly useful as some consumers may object to the idea of consuming viable microorganisms, or giving such viable microorganisms to children or pet animals even though they are assured that such viable microorganisms are beneficial to their health. As the present invention is concerned with increasing compliance with oral care instructions, it is a particular advantage that even such unfounded objections can be taken care of. Thus, unless explicitly mentioned this description and the accompanying examples, figures and claims do not differentiate between viable, thermally inactivated or lyophilized microorganisms.

According to the present invention, thermally inactivated cells preferably are obtained by autoclaving viable microorganism cells at a temperature of 121° C. for at least 20 minutes in the presence of saturated steam at an atmospheric pressure of 2 bar. Such preparation of thermally inactivated microorganisms can be achieved using standard laboratory equipment, as the process of autoclaving is a standard technique known in the art of microbiology and corresponding biotechnological engineering. It is a very fast technique and is proven to inactivate microorganisms of family Lactobacillaceae and particularly of genus *Lactobacillus*.

Alternatively, thermal inactivation of microorganisms according to the present invention can be achieved by freezing such cells to a temperature of −20° C. Such freezing is also easy to perform using standard laboratory equipment.

Regardless of the mode of thermal inactivation, i.e. by autoclaving or by freezing, it is according to the present invention preferred that the concentration of viable microorganisms is reduced by the treatment by at least 85%, 90% or 95%, and particularly preferred by at least 97%, 98%, 99% and more particularly preferred 99.1%, 99.2%, 99.3%, 99.4%, 99.5%, 99.6%, 99.7%, 99.8% or 99.9%. Particularly preferred is such autoclavation or freezing that reduces the concentration of viable microorganisms by at least 3 orders of magnitude (i.e. by a factor of 1000), even more preferably by at least 4 orders of magnitude and even more preferably by at least 5 orders of magnitude.

A particular advantage of the microorganisms of the present invention is that they retain their usefulness as sensorically neutral oral care agents, preferably anti-dental calculus agent, anti-caries and/or anti-oral-malodor agents even after such inactivation by autoclaving or freezing. In such thermally inactivated form, the microorganisms of the present invention are particularly easy to store even at 20° C. in a standard atmosphere having 80% relative humidity at this temperature. This storability is of particular importance, as the inactivated microorganisms according to the present invention allow to produce foods or feeds comprising such inactivated forms without corrupting the "best before" date.

The same advantages can be obtained according to the present invention by using lyophilized microorganisms of the present invention, i.e. lyophilized microorganisms of family Lactobacillaceae and particularly lyophilized lactic acid microorganisms of genus *Lactobacillus*. Lyophilization according to the present invention is preferably for at least 2 hours at room temperature, i.e. at a temperature between 16° C. and 25° C.

In addition to or alternatively to microorganisms of the present invention, for example in viable, thermally inactivated or lyophilized form, fragments thereof can be used. A fragmentation of microorganisms can be easily performed using standard methods known in the art, particularly by cell lysis and/or pasteurization. The method used for lysing or fragmenting a microorganism according to the present invention including thermally inactivated and/or lyophilized forms thereof is of no particular concern. Appropriate methods can be chosen for example among chemical methods including enzymatic treatment, preferably by one or more proteases, for example by proteinase K, lipases or glycosidases; non-limiting examples for other chemicals are ionophores, detergents, for example sodium dodecyl sulfate, acids or bases; non-limiting examples of physical means are high pressure, like French-pressing, osmolarity and milling for example using glass or iron beats. Particularly preferred methods for producing thermally inactivated and/or lyophilized microorganisms according to the present invention and fragments thereof are described in WO 2006/027265 A1, pages 25-28 and WO 2009/149816 A1, pages 28-34. "A fragment of the microorganism of the present invention" encompasses any part of the cells of the microorganism of the present invention. Preferably, said fragment is a membrane fraction obtained by a membrane-preparation. Membrane preparations of binder microorganisms belonging to the family of Lactobacillaceae, preferably to the genus of *Lactobacillus*, can be obtained by methods known in the art, for example, by employing the method described in Rollan et al. Int. J. Food Microbiol. 70 (2001), 303-307, Matsuquchi et al, Clin. Diagn. Lab. Immunol. 10

(2003), 259-266 or Stentz et al. Appl. Environ. Microbiol. 66 (2000), 4272-4278 or Varmanen et al. J. Bacteriology 182 (2000), 146-154. Alternatively, a whole cell preparation is also envisaged. Preferably, the herein described fragment of the binder microorganism of the present invention retains the capability of specifically binding to a *mutans Streptococcus* and more preferably *Streptococcus mutans*, which is described in detail herein.

The microorganisms used in the present invention, i.e. lactic acid bacteria preferably of family Lactobacillaceae or of genus *Lactobacillus* including respective thermally inactivated or lyophilized forms thereof and fragments thereof, are preferably used as anti-caries agents. According to the present invention, the term "anti-caries agent" is defined as any agent which, by its mere presence in the oral cavity of a human or animal including pet animals like dogs, cats, rats, mice, hamsters, guinea pigs or monkeys, reduces the risk of developing new cariotic lesions. It is a particular advantage of the present invention that the microorganism used as anti-caries agent does not have to be antimicrobially effective on its own. Thus, it is not necessary according to the present invention that microorganisms or fragments thereof used as anti-caries agents reduce in a co-cultivation the number of caries-generating microorganisms, particularly microorganisms belonging to the group of *mutans Streptococci*.

It is therefore another advantage according to the present invention that the microorganisms used as anti-caries agents have a very limited impact on the normal microflora of the oral cavity of a human being or of an animal, particularly a pet animal. Suitable microorganisms will be described below.

The microorganism used in the present invention, i.e. lactic acid bacteria preferably of family Lactobacillaceae or of Genus *lactobacillus*, including respective thermally inactivated or lyophilized forms thereof and fragments thereof, are preferably used as anti-dental calculus agents. According to the present invention, the term "anti-dental calculus agent" is defined as any agent which, by its mere presence in the oral cavity of a human or animal including pet animals, reduces the risk of developing dental calculus, or which slows down further development of dental calculus. It is not required that the anti-dental calculus agent of the present invention actually removes dental calculus already formed on a tooth.

Also, the microorganisms used in the present invention, i.e. lactic acid bacteria preferably of family Lactobacillaceae or of Genus *lactobacillus* including respective thermally inactivated or lyophilized forms thereof and fragments thereof, are preferably used as anti-oral malodor agents. According to the present invention, the term "oral malodor" indicates any unpleasant smell originating in the oral cavity. The term thus is used according to the present invention both for weak forms of malodor, also termed "bad breath", which are not considered an illness, and also for such forms of malodor which, for example due to their intensity or scent, are considered to be the symptom of an illness; such latter forms of oral malodor are also called halitosis. Clinically relevant forms of oral malodor, i.e. halitosis, can have various causes. Most notable for all forms of oral malodor are infections by microorganisms colonizing the oral cavity, wherein such microorganisms digest organic material, for example dead epithelial cells, other microorganisms or residual food or feed. Preferably, the present invention is set to delay onset of oral malodor, and/or to reduce the intensity or alter the scent of oral malodor, be it clinically not relevant bad breath or clinically relevant halitosis. However, unless explicitly mentioned herein, the term "oral malodor" does not cover malodors originating beyond the oral cavity, e.g. in the esophagus or stomach. Such malodors may for example become noticeable during eructation.

Within the present invention, the term "oral cavity" indicates that cavity which extends from lips and teeth up to but not including the uvula.

The mouth defines the oral cavity of mammals, preferably humans or animals such as pets, composed by the oral mucosa (gums, lips, cheeks, palate and floor of the mouth), the tongue and the teeth (including artificial structures).

Also according to the present invention, the term "sensorically neutral" is defined as such agent which can replace up to 2 wt.-% of wholemeal wheat flour such that at most 5 out of 10 trained panelists will consider the taste and scent of such mixture of wholemeal wheat flour and microorganisms and/or fragments according to the invention to be noticeably altered, judging on the basis of a scale ranging from no difference, slightly altered, noticeably altered to clearly altered. Preferably, up to 5 wt.-% of wholemeal wheat flour can be replaced by the microorganisms and/or fragments thereof such that at most 5 out of 10 panelists consider the taste and/or scent of such mixture to be noticeably altered.

According to the invention, there is thus also provided a composition comprising a binder microorganism or fragment thereof in an amount
        both (a) sensorically neutral and (b) effective for reducing *mutans Streptococci* in the oral cavity of a human or animal and/or effective for reducing oral malodor, wherein the microorganism is a lactic acid bacterium.

It has now surprisingly been found that to exert an anti-caries effect by a sensorically neutral agent, it is sufficient to use a binder lactic acid bacterium for reducing *mutans Streptococci* in the oral cavity. As described above, such binder lactic acid bacteria, thermally inactivated or lyophilized forms thereof and also fragments of such binder lactic acid bacteria can be used as anti-caries agent without having an anti-microbial effect, i.e. without killing cariogenic microorganisms themselves or repressing their growth. Instead, it is sufficient that a binder microorganism or fragment thereof binds to one or more species of *mutans Streptococci*. Such binding can lead to an agglutination of bound *mutans Streptococci*, which in turn are removed from the oral cavity by normal swallowing of saliva and during eating and drinking. As described in WO 2008/074473 A2 removal of *mutans Streptococci* from the oral cavity significantly reduces the risk of biofilm formation in the oral cavity and on teeth, thereby indirectly reducing the risk of developing caries. This particularly holds true also for such binder microorganisms which bind to *Streptococcus mutans*, as described in WO 2006/027265 A1. However, it had not been known so far that such binder microorganisms could be used as sensorically neutral agents, i.e. in a sensorically neutral concentration as described above and detailed hereinafter. Also, it had not been known so far that such binding to *mutans Streptococci* and particularly to *Streptococcus mutans* could reduce the risk of development of oral malodor.

According to the invention, a composition is thus preferred comprising a microorganism or fragment thereof that is capable of specifically binding to a bacterium belonging to the group of *mutans Streptococci*, wherein the specific binding is
(i) resistant to heat treatment; and/or
(ii) resistant to protease treatment; and/or
(iii) calcium-dependent; and/or (iv) formed within a pH range between 4.5 and 8.5; and/or
(v) formed in the presence of saliva.

The term "specifically binding" in the context of the present invention means that the binder microorganism or fragment thereof, preferably a microorganism (or corresponding fragment) belonging to the family of Lactobacillaceae and more preferably of genus *Lactobacillus*, binds to one or more strains belonging to *mutans Streptococci*, preferably to *Streptococcus mutans*, but does not bind to most other, preferably to no other species belonging to the genus *Streptococcus*. Namely, the binder microorganism or fragment thereof does preferably not bind to bacteria belonging to the species of *Streptococcus oralis* and/or *Streptococcus mitis* and/or *Streptococcus sanguinis*. Even more preferably, the binder microorganism also does not bind to bacteria belonging to the species of *Streptococcus salivarius*, more preferably belonging to the subspecies *thermophilus*. More preferably, the binder microorganism or fragment thereof does not bind to *Streptococcus oralis* DSMZ 20066, *Streptococcus oralis* DSMZ 20395, *Streptococcus oralis* DSMZ 20627, *Streptococcus mitis* DSMZ 12643 and/or *Streptococcus sanguinis* DSMZ 20567. And even more preferably, the binder microorganism or fragment thereof also does not bind to *Streptococcus salivarius* ssp. *thermophilus*, The specific binding reaction comprises binding and, preferably, aggregating *Streptococcus mutans* or other *mutans Streptococci* cells as described herein by the binder microorganism of the present invention including a fragment thereof in the mouth. This specific binding leads, in consequence, to flushing away the boud cells by, for example, salivary flow or by a mouth rinse or mouth wash and the like as described herein. Preferably, the specific binding reaction of the binder microorganisms of the present invention and their fragments to *Streptococcus mutans* and/or other *mutans Streptococci* prevents such *Streptococcus* cells from attaching to the surface of a tooth or teeth, or, while not being bound by such theory, could lead to detachment of *Streptococcus* cells from the surface of a tooth or teeth. In consequence, the specific binding reaction results in flushing away bound *Streptococcus* cells out of the mouth, thereby diminishing a causative agent of biofilm formation and, thus, preventing and/or treating caries.

It is believed that the binder microorganism or fragment thereof may bind specifically to the streptococcal antigen I/II which is also known as antigen B, IF, P1, SR, MSL-1 or PAc. However, the binder microorganism or fragment thereof may bind to any other protein or surface structure of *S. mutans*, thereby aggregating *S. mutans* and flushing it out of the oral cavity as described herein. It is known that *Streptococcus* mutants binds via said streptococcal antigen I/II to the pellicle. Accordingly, when the binder microorganism of the present invention may bind, for example, to said streptococcal antigen I/II, *Streptococcus mutans* or another respective *mutans Streptococcus* is hampered to bind to the surface of teeth which thus helps to prevent and/or treat caries.

The pellicle is a clear, thin covering containing proteins and lipids found in saliva. It is formed within seconds after a tooth surface is cleaned. Pellicle formation is the first step in dental plaque formation. Dental plaque is a soft deposit that accumulates on the teeth. Plaque can be defined as a complex microbial community, with greater than $10^{10}$ bacteria per milligram. It has been estimated that as many as 400 distinct bacterial species may be found in plaque. In addition to the bacterial cells, plaque contains a small number of epithelial cells, leukocytes, and macrophages. The cells are contained within an extracellular matrix, which is formed from bacterial products and saliva. The extracellular matrix contains protein, polysaccharide and lipids. One of the proteins present in saliva is agglutinin which is on the one hand thought to lead to a partial removal of *mutans Streptococci* from the mouth, however, is on the other hand suspected to facilitate adhesion of *mutans Streptococci* to the surface of teeth, thereby facilitating the initial attachment of *Streptococcus* cells to teeth and, thus, onset of caries.

Preferably, the above mentioned binder microorganism belonging to the group of lactic acid bacteria—or fragment thereof—is capable of specifically binding to *Streptococcus mutans* serotype c (DSMZ 20523) and/or serotype e (NCTC 10923) and/or serotype f (NCTC 11060) and/or *Streptococcus sobrinus* DSMZ 20742 and/or *Streptococcus ratti* DSMZ 20564 and/or *Streptococcus cricetus* DSMZ 20562 and/or *Streptococcus ferus* DSMZ 20646 and/or *Streptococcus macacae* DSMZ 20714.

This means that the above mentioned binder microorganism belonging to the group of lactic acid bacteria, or its fragment, preferably binds to at least one microorganism selected from the group consisting of *Streptococcus mutans* serotype c (DSMZ 20523), serotype e (NCTC 10923), serotype f (NCTC 11060), *Streptococcus sobrinus* DSMZ 20742, *Streptococcus ratti* DSMZ 20564, *Streptococcus cricetus* DSMZ 20562, *Streptococcus ferus* DSMZ 20646 and *Streptococcus macacae* DSMZ 20714. More preferably, the above mentioned binder microorganism belonging to the group of lactic acid bacteria or fragment thereof binds to any combination, grouping or subgrouping of the above mentioned bacteria. Even more preferably, the above mentioned binder microorganism or fragment thereof belonging to the group of lactic acid bacteria binds to all of the above mentioned bacteria. In accordance with the present invention a "serotype" is an antigenic property of a bacterial cell, preferably of a *Streptococcus mutans* or *Streptococcus sobrinus* cell, identified by serological methods known in the art.

As described above, the specific binding of the binder microorganism or fragment thereof to *mutans Streptococci* and preferably to *Streptococcus mutans* is preferably resistant to heat treatment. Accordingly, binding is not abolished when the binder microorganism of the present invention is treated with heat, for example, at a temperature above 55° C., even more preferably of more than 65° C., particularly preferred of more than 95° C. and most preferred at 121° C. After cooling down, the capability of the binder microorganism of the present invention or its fragment to specifically bind *mutans Streptococci* is determined as described herein.

The corresponding temperature can depend on the specific binder microorganism species but can be easily determined by the skilled person by routine experimentation, e.g. by incubating the corresponding cells at different temperatures and determining the amount of binder cells or fragments thereof which is still capable of specifically binding to *mutans Streptococci* and/or *Streptococcus mutans* by using methods as those shown herein. Generally, the heat treatment should last for a period of time of at least 1 minute. Preferably, the heat treatment lasts for a period of time of at least n minutes, wherein n is an integer in the range of 2 to 60, with n=20 being particularly preferred. However, there is in principle no upper limit for the time of incubation. However, it is preferably no longer than 4, 3, 2 or 1 hour(s). The most preferred heat treatment is at least 20 minutes at a temperature of 121° C. in a saturated steam having an atmospheric pressure of 2 bar. Thus, the thermally inactivated form of the binder microorganism of the present invention obtainable by autoclaving is particularly preferred. The most preferred heat treatment is considered as abolishing any function of a protein and of any vitality of cells which thus distinguishes the microorganism of the present invention from other microorganism in that it is still capable of the specifically binding to *S. mutans*. Hence, it is very useful for any food, feed, drink or composition of the present invention if it is desired that the microorganism should not be alive.

The specific binding of the binder microorganism or its fragment is furthermore preferably characterized by its resistance to protease treatment. Preferably, the binding is resistant to treatment with one or more proteases selected from the group consisting of pronase E, proteinase K, trypsin and chymotrypsin. These proteases show no specificity and, thus, are considered as degrading any protein being on the cell surface of a microorganism. Other proteases, which are known to have preferences for certain patterns of amino acid residues, are elastase elastase, thrombin, aminopeptidase I, carboxypeptidase, dostripain, endoproteinase, papain, cathepsin B, pepsin, gastricsin, chymosin, cathepsin D. The latter proteases could also be used to test whether the specific binding of the binder microorganism or fragment thereof to *S. mutans* or another *mutans Streptococcus* is resistant to the latter more specific proteases. Thus, after protease treatment which is described in the examples of WO 2008/074473 A2 or WO 2006/027265 A1, which are incorporated herein, the binder microorganism or fragment is still capable of specifically binding to *Streptococcus mutans/mutans Streptococci*.

In addition, the specific binding of the binder microorganism or fragment is furthermore preferably characterized by its dependency on calcium. Preferably, the specific binding takes place in the presence of a concentration of calcium ions between 0.05 mM and 500 mM, preferably between 1 mM and 100 mM. Particularly preferred the calcium concentration is between 2 mM and 30 mM. The dependency of the specific binding on calcium can be tested as described in the examples of WO 2008/074473 A2 or WO 2006/027265 A1, which are incorporated herein. Moreover, the specific binding to the binder microorganism or fragment is preferably maintained over a pH range between 4.0 and 9.0, preferably between 4.0 and 7.0 In particular, the pH value at which the specific binding takes still place is preferably 4.5. Assaying of the maintenance of the specific binding over the pH range described above is shown in the above mentioned examples.

The specific binding is preferably independent of magnesium. Thus, it is not necessary that magnesium ions or magnesium salts are present.

Another preferred characteristic of the specific binding is its occurrence in the presence of saliva. Saliva is an exogenous secrete which is synthesized by the salivary glands. It is a complex liquid containing, apart from about 99% water a multiplicity of organic and inorganic compounds. Physiological ingredients of saliva are, inter alia, enzymes, e.g., amylases, carboanhydrases, lysozyme, peroxidases or proteins, e.g., mucins, lactoferrin, proline-rich proteins, cystatines, histatines or statherines or soluble IgA. Thus, although a variety of potentially interfering substances are present in saliva, the specific binding of the microorganism of the present invention was not disturbed or hampered. For testing the specific binding in the presence of saliva, it is preferred that saliva is used which contains preferably the *Streptococcus* species described above. If, however, *Lactobacillus rhamnosus* species are tested for specific binding to *S. mutans* in the presence of saliva, it is preferred that *Streptococcus salivarius* ssp. *thermophilus* is omitted. The specific binding is assayed as described herein. The aforementioned characteristics of the binder microorganism or fragment thereof belonging to the group of lactic acid bacteria renders it to be a robust and effective agent for preventing and/or treating caries since it is mainly administered in various forms to the mouth including the oral cavity and teeth where, inter alia, saliva including certain proteases and low pH values after ingestion of carbohydrate containing food stuff is present. Moreover, the resistance to heat has beneficial effects in adding the microorganism of the present invention as additive to food or feed during the preparation of said food or feed. Namely, food or feed is often heat sterilized, pre-cooked, pasteurized and the like which is detrimental for viability of microorganisms.

The binder microorganism of the present invention, and/or the corresponding fragment thereof, is capable of specifically binding to one or more *mutans Streptococci* and preferably to *Streptococcus mutans*, wherein the specific binding is
(i) resistant to heat treatment, and
(ii) resistant to protease treatment, and
(v) formed in the presence of saliva.

Such binder microorganisms and fragments thereof combine the aforementioned advantages. In particular, since their specific binding is resistant to heat treatment, they can be incorporated in a product that is heat treated for sterilization, thereby prolonging shelf life of the product without corrupting the oral health properties conferred to the product by the microorganisms of fragment thereof, preferably without corrupting the anti-dental calculus effectiveness, the anti-caries effectiveness or the anti-oral malodor effectiveness of the product. Also, due to the protease resistance the binder microorganisms and fragments can be incorporated in various products of different composition even before such products are heat treated for protein denaturation. And importantly the formation of a specific binding in the presence of saliva allows to use the binder microorganisms and fragments thereof also in such products which do not drain saliva from the oral cavity.

This ability in turn increases consumer compliance, particularly in children and animals including pet animals, as such consumers tend to be reluctant to use a product which would lead to a dry oral cavity.

For these reasons, the binder microorganism of the present invention, and/or the corresponding fragment thereof, is even more preferably capable of specifically binding to one or more *mutans Streptococci* and preferably to *Streptococcus mutans*, wherein the specific binding is
(i) resistant to heat treatment for 20 minutes at a temperature of 121° C. in a saturated steam having an atmospheric pressure of 2 bar, and
(ii) resistant to treatment by one or more enzymes selected from pronase E, proteinase K, trypsin and chymotrypsin, and
(v) formed in the presence of saliva.

Preferably, the specific binding of the binder microorganism of the present invention, and/or the corresponding fragment thereof is also
(iii) calcium-dependent, and
(iv) formed within a pH range between 4.5 and 8.5.

The method to determine the binding of binder microorganisms and fragments thereof to *mutans Streptococci* is described in Lang et al (2010) Journal of Dental Research 89(2) 175-179, which is incorporated herein.

Preferably, the specific binding of the binder microorganism or fragment thereof can be assayed as follows:
(a) growing said binder microorganism to stationary phase, or, in case a fragment is to be tested, obtaining such fragment,
(b) mixing said binder microorganism or fragment with a *mutans* Streptococcus which has been grown to stationary phase,
(c) incubating the mixture obtained in step (b) under conditions allowing the formation of aggregates of said microorganism and said *Streptococcus*, and
(d) detecting aggregates by the occurrence of a pellet.

In a preferred embodiment the bacterium belonging to the group of *mutans Streptococci* used in such an assay is *Streptococcus mutans*. For a specific binding to *mutans Streptococci*, preferably no binding can be detected to at least one, preferably at least two and more preferably at least three and even more preferably all microorganisms selected from the group consisting of *Streptococcus salivarius* ssp. *thermophilus, Streptococcus oralis* DSMZ 20066, *Streptococcus oralis* DSMZ 20395, *Streptococcus oralis* DSMZ 20627, *Streptococcus mitis* DSMZ 12643 and *Streptococcus sanguinis* DSMZ 20567.

In particular, binder microorganisms belonging to the group of lactic acid bacteria, preferably of family Lactobacillaceae and even more preferably of genus *Lactobacillus*, or corresponding fragments, are preferably mixed with *mutans Streptococci* in cell-to-cell ratios of 3:1 to 60:1 (*mutans Streptococci*:binder microorganism). Both the lactic acid binder bacteria and *mutans Streptococci* are grown in liquid culture to stationary phase. Preferably, the optical density is measured photometrically at a wavelength of 600 nm. The mentioned ratios correspond to a ratio of colony forming units from 1:50 to 1:2.5. Preferably, an OD600=1 in 1 ml corresponds to $3\times10^8$ colony forming units of a *mutans Streptococcus*. Preferably, an OD600=1 in 1 ml corresponds to $7\times10^9$ colony forming units of lactic acid bacteria. Preferably, for assaying the aggregation reaction by pelleting, the bacteria are in a volume of 2 ml in 15 ml Falcon tubes. If necessary, the culture suspensions are diluted with PBS-butter to obtain volumetric ratios mentioned above, while keeping the final volume at 2 ml.

Preferably, the mixture of *Streptococcus* and binder lactic acid bacteria or fragments thereof is vortexed for about 15 seconds and then left undisturbed for at least 5, 10, 15 minutes and more preferably for 20 minutes at room temperature, i.e. any temperature between 16° C. and 25° C. An aggregation is visible as an immediate turbidity of the suspension and, after at least 20 minutes, an aggregation is visible by aggregates that settle as a visible pellet, whereas non-*mutans Streptococcus* aggregating mixtures stay in suspension. As a control, self-aggregation of the respective binder bacterium or fragment and the *mutans Streptococcus* strain can be assayed by omitting either the *mutans Streptococcus* or the binder microorganisms/fragment.

The aggregation of a binder microorganism and a *mutans Streptococcus* according to the above described assay can be quantified by separating the formed aggregates as described by Lang et al (2010) Journal of Dental Research 89(2) 175-179, or by centrifugation, e.g. at 500×g for 30 seconds. Subsequently, the amount of aggregation can be determined by measuring the amount of non-aggregated cells that are left in the supernatant. The determination can be carried out by any suitable means known to the person skilled in the art. Preferably, the determination is carried out by removing a certain volume of the supernatant, e.g. 1 ml. Subsequently, the optical density of the removed supernatant may be measured at any suitable wavelength, known to the skilled person, e.g. at 600 nm. The measured value after subtraction of a value a corresponding control test without lactobacilli represents the amount of cells that have not been aggregated.

A method for determining specific binding according to the present invention is described in example 4 of WO 2008/74473 A2, with corresponding instructions for cultivation of respective microorganisms given in example 1 of that publication. Both examples are incorporated herein for the purpose of disclosing a method for determining specific binding according to the present invention.

Alternatively, in order to address the possible problem of self-aggregation a stain, preferably a fluorescent stain, can be employed. Thus, in a more preferred embodiment, the specific binding can be assayed as follows:
(a) growing said microorganism to stationary phase;
(b) mixing said microorganism with a bacterium belonging to the group of *mutans Streptococci* which has been grown to stationary phase and which has been stained using a suitable stain, preferably a fluorescent stain;
(c) incubating the mixture obtained in step (b) under conditions allowing the formation of aggregates of said microorganism and a bacterium of the group of *mutans Streptococci*; and
(d) detecting aggregates by the detection of the stain, preferably a fluorescencent stain.

Again, in a preferred embodiment the bacterium belonging to the group of *mutans Streptococci* used in such an assay is *Streptococcus mutans*.

Preferably the aggregation assay may be carried out in that first the binder microorganism and *mutans Streptococci* are grown to stationary phase as described above. Preferably, the optical density is measured photometrically at a wavelength of 600 nm. Preferably, an OD600=1 in 1 ml corresponds to $3\times10^8$ colony forming units of a respective *mutans Streptococcus*. Preferably, an OD600=1 in 1 ml corresponds to $7\times10^9$ colony forming units of binder microorganism, particularly of family lactobacillaceae and even more preferably of genus *lactobacillus*, as described herein.

Subsequently, the *mutans Streptococci* are stained. In a further preferred embodiment, the binder microorganisms are stained, whereas the *Streptococci* are not stained. As stain any suitable stain can be used, preferably a fluorescence stain known to the person skilled in the art may be used. Preferably, a specific or unspecific fluorescence stain may be used, for example, CFDA-SE to stain intact cells, other useful stains include carboxyfluorescein diacetate acetoxymethyl ester, BCECF AM and Calcein AM. Specifically, the cells are harvested, e.g. by centrifugation, preferably at 3200×g for 5 min. Subsequently, the obtained pellet may be resuspended in any suitable buffer known the person skilled in the art, preferably in a PBS-buffer. The amount of buffer may be calculated so that the resulting suspension has an OD600 of, e.g., 4.2/ml. Subsequently, the suspension may be mixed with a suitable stain, e.g. a fluorescence stain, preferably with 5,6-carboxyfluorescein diacetate, succhinimidyl ester (CFDA-SE), more preferably with 2 µl of a CFDA-SE solution (Invitrogen). Subsequently, the cells may be incubated for a suitable time period, as known to the skilled person, e.g. for 2 hours, at a suitable temperature as known to the skilled person, for instance, at 37° C. In a further step, the stained cells may be harvested, e.g. by centrifugation. Preferably, the centrifugation is carried out at 3200×g for 5 min. The cells may then be resuspended in a suitable buffer, as known to the person skilled in the art, e.g. in 2 ml of a PBS-buffer.

For the aggregation, binder microorganisms preferably mixed with *mutans Streptococci* in volumetric ratios of 3:1 to 1:3 (*mutans Streptococci*:binder microorganism). More preferably, the volumetric ratio of the mixture is 1:1. The mentioned ratios correspond to a ratio of colony forming units from 1:50 to 1:150. For assaying the aggregation reaction via measuring of staining, preferably of fluorescence, the binder microorganism and the *mutans Streptococci* are used in any suitable volume known to the skilled person, preferably, in a volume of 50 µl. Preferably, the mixture is carried out in a microtiter plate, e.g. in a 96 well microtiter plate. Subsequently, the mixture may be vortexed, preferably for 12 min at full speed. Afterwards, the mixture may be centrifuged, e.g. for 10 seconds at 500×g. The supernatant may then be removed and the pellet may be resuspended in any suitable buffer known the person skilled in the art, preferably in PBS-buffer in any suitable volume, e.g. in 100 µl. The staining of the suspension may be measured in the mixture by any suitable means known to the skilled person. Preferably, in case of fluorescence, the fluorescence may be detected in a fluorescence reader, e.g. at a wavelength of 495 nm for excitation and 525 nm for emission. As controls, binder microorganism alone and stained *mutans Streptococci* alone may be assayed. Any background staining, e.g. fluorescence, may be measured for the tested *mutans Streptococci* alone and may preferably be subtracted from the value for the aggregation with the respective binder microorganism. An aggregation effect is present if the background staining, e.g. fluorescence, measured as indicated herein above, is subtracted from the measured staining, e.g. fluorescence, in a sample containing a binder microorganism as described herein above and a tested *mutans Streptococcus*, as described herein above, and the resulting value is at least above zero. More preferably, an aggregation effect is present if the resulting value is reproducibly above zero in a series of tests, carried out as described herein above. A "series of experiments" means at least 2, preferably 3, more preferably 4 and most preferably 5 tests.

The alternative method of testing binding can be performed as described in example 5 of WO 2008/074473 A2, which is incorporated herein by reference.

For fragments of binder microorganisms, binding is essentially determined as for viable or inactivated binder microorganisms as described above. The amount of fragments to be used for determining binding or for preparing a food or feed composition according to the invention instead of binder microorganism cells is preferably the same as the amount of cell wall material of viable or thermally inactivated binder microorganism. For example, peptidoglycan content of binder microorganism content can be measured by using appropriate dyes, and the same amount of fragments based on such dye measurement can be used.

The above mentioned binder microorganisms are preferably lactic acid bacteria belonging to the genus of *Lactobacillus*, more preferably *Lactobacillus* species as described herein. Even more preferably said *Lactobacillus* belongs to the species of *Lactobacillus paracasei* or *Lactobacillus rhamnosus*. However, the *Lactobacillus* species are not limited thereto. The above mentioned binder microorganisms may preferably be "isolated" or "purified". The term "isolated" means that the material is removed from its original environment, e.g. the natural environment if it is naturally occurring. For example, a naturally-occurring microorganism, preferably a *Lactobacillus* species, separated from some or all of the coexisting materials in the natural system, is isolated. Such a microorganism could be part of a composition, and is to be regarded as still being isolated because in that composition is not part of its natural environment. Thus, a microorganism grown in a pure culture is still considered an isolated microorganism. Likewise, a fragment of a microorganism is considered "isolated" according to the invention if it is separated from at least some material of the respective microorganism.

The term "purified" does not require absolute purity; rather, it is intended as a relative definition. Individual microorganisms obtained from a library have been conventionally purified to microbiological homogeneity, i.e. they grow as single colonies when streaked out on agar plates by methods known in the art. Preferably, the agar plates that are used for this purpose are selective for lactic acid bacteria, and particularly preferably to *Lactobacillus* species. Such selective agar plates are known in the art.

To obtain fragments, it is preferred to rupture viable or thermally inactivated binder microorganism cells by methods known in the art, for example sonication, French press or ball milling, and to separate the fragments from other cell remains by centrifugation. The fragment pellet can then be washed and centrifuged again to obtain a fragments pellet.

More preferably, the above mentioned binder microorganism belonging to the group of lactic acid bacteria is selected from the group consisting of *Lactobacillus paracasei* or *Lactobacillus rhamnosus*, respectively, having DSMZ accession number DSMZ 16667 (*L. paracasei* ssp. *paracasei* Lb-Ob-KI), DSMZ accession number DSMZ 16668 (*L. paracasei* ssp. *paracasei* Lb-Ob-K2), DSMZ accession number DSMZ 16669 (*L. paracasei* ssp. *paracasei* Lb-Ob-K3), DSMZ accession number DSMZ 16670 (*L. paracasei* ssp. *paracasei* Lb-Ob-K4), DSMZ accession number DSMZ 16671 (*L. paracasei* ssp. *paracasei* LbOb-K5), DSMZ accession number DSMZ 16672 (*L. rhamnosus* Lb-Ob-K6) and DSMZ accession number DSMZ 16673 (*L. rhamnosus* Lb-Ob-K7) or a mutant or derivative thereof, wherein said mutant or derivative retains the capability to specifically bind to *mutans Streptococci*. The term "*Lactobacillus paracasei* or *Lactobacillus rhamnosus* having DSMZ accession number" relates to cells of a microorganism belonging to the species *Lactobacillus paracasei* or *Lactobacillus rhamnosus* deposited with the Deutsche Sammlung für Mikroorganismen and Zellkulturen GmbH ("DSMZ") on Aug. 26, 2004 and having the following deposit numbers DSMZ 16667, 16668, 16669, 16670, 16671, 16672 or 16673. The DSMZ is located at the Mascheroder Weg 1b, D-38124 Braunschweig, Germany. The aforementioned DSMZ deposits were made pursuant to the terms of the Budapest treaty on the international recognition of the deposit of microorganisms for purposes of patent procedure.

"A mutant or derivative" of the above mentioned binder microorganism belonging to the group of lactic acid bacteria, preferably of the deposited *Lactobacillus paracasei* or *Lactobacillus rhamnosus* cells, has preferably the same characteristics as the respective deposited strains, i.e. it retains the capability to specifically bind to *mutans Streptococci*, preferably with the binding characteristics as described herein. For example, said derivative can be genetically engineered. In the context of the present invention the term "genetically engineered" is used in its broadest sense for methods known to the person skilled in the art to modify desired nucleic acids in vitro and in vivo such that genetic modifications are affected and genes are altered by recombinant DNA technology. Accordingly, it is preferred that said methods comprise cloning, sequencing and transformation of recombinant nucleic acids. For this purpose appropriate vectors including expression vectors for *Lactobacillus* species as, for example, described in EP 0 506 789 B1, EP 0 316 677 B1, EP 0 251 064 B1, EP 0 218 230 B1, EP 0 133 046 B1 or WO 89/01970.

Primers, enzymes, further host cells for cloning of intermediate constructs and the like can be used and are known by the skilled artisan. Preferably, genetically engineered mutants comprise cells of a binder microorganism belonging to the group of lactic acid bacteria, preferably of the family of lactobacteriaceae, even more preferably of genus *lactobacillus* and most preferably one of the deposited *Lactobacillus* species, harbouring a recombinant nucleic acid either comprised in their bacterial chromosome or on one or more plasmids or comprised in their bacterial chromosome and/or one or more plasmids. Said recombinant nucleic acids are preferably foreign to the above mentioned binder microorganism belonging to the group of lactic acid bacteria. By "foreign" it is meant that the polynucleotide or nucleic acid molecule is either heterologous with respect to the host cell, this means derived from a cell or organism with a different genomic background, or is homologous with respect to the host cell but located in a different genomic environment than the naturally occurring counterpart of said nucleic acid molecule. In this case the heterologous polynucleotide may be either under the control of its own promoter or under the control of a heterologous promoter. The above described vector or nucleic acid molecule, which is present in the host cell may either be integrated into the genome of the host cell or it may be maintained in some form extrachromosomally. In this respect, it is also to be understood that the above described nucleic acid molecule can be used to restore or create a mutant gene via homologous recombination. Plasmids may be low, medium or high copy number plasmids. Said genetically engineered mutants may harbour nucleic acids encoding a glucanase or mutanase which is capable of degrading the mutan specific 1,3-glycosidic bond of saccharose subunits. Fungal glucanases are, for example, described in Fuglsang et al., J. Biol. Chem. 275 (2000), 2009-2018. It is also envisaged that genetically engineered mutants comprise cells harbouring recombinant nucleic acids encoding antibodies which are preferably secreted or anchored in the bacterial cell wall. The term "antibody" encompasses intact antibodies as well as antibody fragments thereof, like, separated light and heavy chains, Fab, Fab/c, Fv, Fab', F(ab')2. The term "antibody" also comprises humanized antibodies, bifunctional antibodies and antibody constructs, like single chain Fvs (scFv) or antibody-fusion proteins. It is also envisaged in context of this invention that the term "antibody" comprises antibody constructs which may be expressed in cells of the derivative of the above mentioned deposited microorganism, e.g. antibody constructs which may be transformed via, inter alia, vectors by methods known in the art. It is in particular envisaged that such antibody constructs specifically recognize, for example, the streptococcal antigen I/II. Such an approach is, for example, described in Krueger et al., Nat. Biotechnol. 20 (2002), 702-706 or Shiroza, Biochim Biophys Acta 1626 (2003), 57-64.

Secretion of the expressed antibody is preferably achieved by operatively linking the nucleic acid encoding an antibody to a secretion signal sequence. Anchoring in the bacterial cell wall could be achieved by making use of the mechanism of the enzyme sortase. Namely, surface proteins of gram-positive bacteria are linked to the bacterial cell wall by a mechanism that involves cleavage of a conserved Leu-Pro-X-Thr-Gly (LPXTG) motif and that occurs during assembly of the peptidoglycan cell wall. Accordingly, the nucleic acid molecule encoding an antibody may be fused to a sequence encoding the aforementioned conserved motif, which is used by sortase to anchor proteins in the bacterial cell wall.

It is also envisaged that the above mentioned binder microorganism belonging to the group of lactic acid bacteria be genetically modified to harbor a nucleic acid molecule encoding reuterin which is an antimicrobial substance effective, inter alia, against *Streptococcus mutans*. Reuterin is, for example, described in Talarico et al., Chemother. 33 (1989), 674-679.

A mutant of the binder microorganism belonging to the group of lactic acid bacteria, preferably a mutant of the deposited *Lactobacillus* strains, is preferably artificially mutated. In accordance with the present invention, the term "mutated" means one or more permanent modifications of genetic material, i.e. nucleic acids, caused, for example, naturally or by physical means or chemical compounds/substances/agents, such as EMS or ENU. Said modifications include point mutations, like transitions or transversions, deletion/insertion/addition of one or more bases within a nucleic acid/gene/chromosome thereby modifying the nucleic acid/gene/chromosome which can cause, inter alia, aberrant gene expression/transcription/translation or inactive gene products, constitutive active/inactive gene products leading to e.g. dominant-negative effects. Preferably, a mutation leads to in increased capability of specifically binding *mutans Streptococci*. Thus, it is also preferred that the mutant cells of the deposited microorganism which harbour one or more mutations in one or more desired genes or in which one or more mutations in one or more desired genes is induced by methods known to the person skilled in the art. It is also known in the prior art that mutated or genetically engineered bacterial cells can be selected by any suitable method/phenotype. In the context of the present invention, a mutant having an increased capability to specifically bind to *mutans Streptococci* can be tested in accordance with the methods described above. The term "mutant", however, also includes cells of above mentioned binder microorganism belonging to the group of lactic acid bacteria, preferably cells of the deposited microorganism, which harbour naturally-occurring, spontaneous mutations in their genome, i.e. bacterial chromosome. "Spontaneous mutations" are mutations that arise naturally, i.e., without direct genetic manipulation by man, or by exposure to a mutagen. Selection of spontaneous mutants can be accomplished by culturing the strain and selecting the desired variants by, for example, the variant bacterium's capability to show an improved binding to *mutans Streptococci*. Methods for selection of spontaneous mutants are well known in the art (see, for example, Sambrook, Russell "Molecular Cloning, A Laboratory Manual", Cold Spring Harbor Laboratory, N. Y. (2001); Ausubel, "Current Protocols in Molecular Biology", Green Publishing Associates and Wiley Interscience, N.Y. (1989)). For example, such mutations may occur during cultivation, for example, during the normal cell division process coupled with DNA replication or during passaging and/or preserving the mutant of the above mentioned binder microorganism belonging to the group of lactic acid bacteria.

However, even though genetic manipulation of microorganisms may impart beneficial or even highly beneficial properties to the microorganisms, it is alternatively preferred that the binder microorganism and preferably all microorganisms used according to the present invention is not a genetically modified microorganism as defined in Article 2(2) of Directive 2001/18/EC in the respective version applicable at the filing day of this application. However, microorganisms obtained through the techniques of genetic modification listed in Annex 1B to said Directive 2001/18/EC according to the invention are preferably not considered a genetically modified microorganism as defined in Article 2 (2) of Directive 2001/18/EC. By excluding genetically modified microorganisms, rational and irrational fears of consumers can be avoided, thereby increasing consumer compliance with oral healthcare instructions.

According to the present invention the binder microorganism, preferably of the Lactobacillaceae family and even more preferably of genus *lactobacillus*, most preferred one of the above mentioned particularly preferred strains, does not comprise genetic material which has been altered in a way that does not occur naturally by mating and/or natural recombination. Such techniques include (1) recombinant nucleic acid techniques involving the formation of new combinations of genetic material by the insertion of nucleic acid molecules produced by whatever means outside an organism, into any virus, bacterial, plasmid or other vector system and their incorporation into a host organism in which they do not naturally occur but in which they are capable of continued propagation;
(2) techniques involving the direct introduction into an organism of heritable material prepared outside the organism including micro-injection, macro-injection and micro-encapsulation;
(3) cell fusion including protoplast fusion or hybridization techniques where life cells with new combinations of heritable material are formed through the fusion of two or more cells by means of methods that do not occur naturally.

Natural processes such as conjugation, transduction and transformation, however, are preferably not excluded according to the present invention. Further preferably not excluded techniques according to the present invention are, on the condition that they do not involve the use of recombinant nucleic acid molecules or genetically modified organisms other than those produced by one or more of the techniques/methods listed hereinafter are (1) mutagenesis by spontaneous or induced spontaneous mutation, and
(2) cell fusion including protoplast fusion of microorganisms which can exchange genetic material through traditional breading methods.

According to the invention, it is thus preferred that the binder microorganism and preferably also any other microorganism used according to the present invention does not comprise genetic material of an organism of super kingdom archaea or eukaryota, of course with the exception of such genetic material which can naturally be found in strains of the same species or, less preferably, at least in the same genus as the microorganism used according to the present invention. Further preferably, the microorganism used according to the present invention does not comprise genetic material of a microorganism found only in a phylum other than firmicutes and even more preferably does not comprise genetic material found only in or taken from microorganisms of a class other than bacilli, even more preferably does not comprise genetic material only found in or taken from microorganisms of an order other than Lactobacillales.

Where the microorganism used according to the present invention and particularly the binder microorganism is of family Lactobacillaceae, then it is preferred that the respective microorganism does not comprise genetic material found only in or taken from microorganisms of a family other than Lactobacillaceae. Even more preferably, if the microorganism of the present invention and particularly the binder microorganism is of genus *lactobacillus*, then the respective microorganism does not comprise genetic material found only in or taken from microorganisms of a genus other than *lactobacillus*.

The composition according to the invention preferably is preferably an anticariogenic food or feed composition, or an anticariogenic pharmaceutical composition. The present invention thus relates to the use of the above mentioned binder microorganism or fragment thereof for the preparation of an anticariogenic composition, preferably a pharmaceutical or cosmetic composition, for the treatment or prevention of caries caused by *mutans Streptococci* and/or *Streptococcus mutans*.

The term "composition", as used in accordance with the present invention, indicates to compositions which comprise at least one binder microorganism—possibly in thermally inactivated or lyophilized form—or fragment thereof, preferably a deposited microorganism as described above—possibly in thermally inactivated or lyophilized form—or a fragment of said microorganism. It is envisaged that the compositions as used in accordance with the present invention comprise the aforementioned ingredients in any combination. It may, optionally, comprise at least one further ingredient suitable for preventing and/or treating caries. Accordingly, it may optionally comprise any combination of the hereinafter described further ingredients. The term "ingredients suitable for preventing and/or treating caries" encompasses compounds or compositions and/or combinations thereof which either inhibit the binding of *mutans Streptococci* to the surface of teeth, to pellicles and/or which inactivate *mutans Streptococci*. More preferably, said term encompasses compounds or compositions and/or combinations thereof which may inhibit the adhesion of *mutans Streptococci* to the surface of teeth, inhibit the activity of glycosyltransferases of *mutans Streptococci*, inhibit or inactivate *mutans Streptococci*, inhibit the agglutinin-dependent binding of *mutans Streptococci* and/or inhibit the saccharose-dependent binding of *mutans Streptococci* as will be described below.

The composition of the present invention preferably is a composition for oral health of a pet animal, and even more preferably is a composition for prevention or reduction of dental calculus. Such compositions are known for example from EP 01 41 645 A2, WO 0150882 A2, WO 2001/070043 A2, WO 02/078462 A1, WO 2004/082518 A2, WO 2005/092087 A2 and WO 2010/052467 A2. The foods and feeds described in these documents and particularly in the examples mentioned in these documents are incorporated herein as examples of preferred base compositions. These base compositions according to the invention are further amended by incorporating a binder microorganism of the present invention or fragment thereof.

It is a particular advantage of the present invention that by the action of a binder microorganism or fragment thereof, i.e. by specifically binding to a *mutans Streptococcus* and most preferably by specifically binding *Streptococcus mutans*, the build-up of dental calculus can be delayed or slowed down without having to rely on the action of bactericidal agents or other chemical agents which would kill microorganisms in the oral cavity. It is suspected that the normal oral microflora is beneficial for humans and animals, for example as such microorganisms of the normal microflora will compete with pathogens for nutrition, thereby limiting the growth of pathogens and avoiding infections. The present invention allows to let the normal oral microflora remain largely undisturbed and still confers oral care properties, preferably the prevention or slow down of dental calculus formation.

Another advantage of the present invention in the prophylaxis and treatment of dental calculus is that the present invention does not require the presence of decalcifying agents like zinc sulfate, soluble pyrophosphates, sodium tripolyphosphate and soluble diphosphonates. Such agents sequester calcium from the oral cavity, thereby removing a key component of dental calculus formation. However, tooth enamel is largely made up of hydroxyl apatite, which is a mineral with high calcium content. Thus, removal of calcium from the oral cavity is implicated in further weakening of teeth, which is undesired. The present invention, on the other hand, allows to treat or prevent formation of dental calculus without sequestering calcium which would be required for maintenance of healthy tooth enamel.

For best results in the prevention of dental calculus formation, a composition of the present invention therefore comprises a binder microorganism or fragment thereof, wherein the binder microorganism preferably is of family Lactobacillaceae, more preferably of genus *Lactobacillus* and most preferably is one of the above mentioned deposited strains of binder microorganisms, and further comprises decalcifying agents in a concentration such that binding of binder microorganisms or fragments thereof to *mutans Streptococci* is reduced by at most 10% as determined by nephelometry, and preferably does not comprise such agents. In such preferred compositions, decalcifying agents preferably are selected from the group of zinc sulfate, zinc chloride, soluble pyrophosphates, sodium tripolyphosphate and soluble diphosphonates.

The present invention also provides the use of a binder microorganism or fragment thereof as described above for the preparation of a medicament for prevention or treatment of dental calculus, preferably in a child or in a pet animal. As indicated above, the binder microorganism can also be in a thermally inactivated form, particularly in an autoclaved form, or in a lyophilized form. The binder microorganism preferably is of the family of Lactobacillaceae, even more preferably of genus *Lactobacillus*, even more preferably of species *Lactobacillus paracasei* or *Lactobacillus rhamnosus*. Particularly, the binder microorganism of the present invention can be selected from the above indicated strains of *L. paracasei* or *L. rhamnosus*, respectively, having any DSMZ accession number of 16667 to 16673, or a mutant or derivative thereof.

Most preferably, the composition according to the present invention is a food or feed composition, particularly for children or pet animals. Such oral health food or feed compositions are sometimes termed functional food or functional feed. The terms "food" and "feed" are used according to the invention regardless of the nutritional value of corresponding compositions and are thus not limited to particular nutritional purposes, even though food and feed compositions according to the present invention can be tailored to such particular purposes. The terms "food" and "feed" thus indicate that the respective composition is suitable for being placed in the oral cavity and for ingestion.

Of particular importance according to the present invention are food or feed compositions for animals, preferably for pet animals, and most preferably for cats, dogs, rats, hamsters and guinea pigs. In such animals, the formation of caries is particularly notorious and also difficult to treat, as any dental treatment like removal of dental calculus requires anaesthesis of the pet. The present invention is thus particularly suitable for preventing the need for such stressful treatment.

The feed composition of the present invention preferably is a pet feed, i.e. a composition for an animal fed, bred or kept, but not normally used for human consumption in the European Community. Preferably, "pet" according to the present invention is a mammal of order carnivora, even more preferably of suborder caniformia or suborder feliformia, and most preferably of the canidae or felidae family. Further preferred pets are of the order rodentia, wherein particularly preferred animals are mice, rabbits, hamsters and guinea pigs.

For pet feed it is preferred that the compound of the present invention is a compound feed, a complete feed, a complementary feed or a mineral feed. According to the present invention, the term "compound feed" means a mixture of at least two feed materials, whether or not containing feed additives, for oral animal feeding in the form of complete or complementary feed. The term "complete feed" means compound feed which, by reason of its composition, is sufficient for a daily ration. The term "complementary feed" according to the invention means compound feed which has a high content of certain substances but which, by reason of its composition, is sufficient for a daily ration only if used in combination with other feed. The term "mineral feed" means complementary feed containing at least 40% crude ash. Finally, the term "feed material" according to the invention means products of a vegetable or animal origin, whose principal purpose is to meet animal nutricial meads, in their natural state, fresh state or preserved, and products, derived from the industrial processing thereof, and organic or inorganic substances, whether or not containing feed additives, which are intended for use in oral animal feeding either directly as such or after processing, or in the preparation of compound feed, or as carrier of pre-mixtures. The term "oral animal feeding" means the introduction of feed into an animal gastrointestinal tract through the mouth with the aim of meeting the animal's nutritional needs and/or maintaining the productivity of normally healthy animals.

According to the present invention, the composition comprising the binder microorganism can also be a oral health composition. Preferred examples of oral care compositions according to the present invention are tooth paste, dentrifices, tooth powders, topical oral jelly, mouth rinses, denture products, mouth sprays, lozenges, oral tablets, chewing gum, dental floss or dental tape, and particularly for animals, chew products.

A preferred oral care composition according to the present invention comprises not only the binder microorganism or fragment thereof, but also an orally acceptable carrier, such carrier can be any suitable vehicle which can be applied to the oral cavity in a safe and effective manner, such that the binder microorganism of the present invention and/or the fragment thereof can bind to one or more strains of *mutans Streptococci* and preferably to one or more strains of *Streptococcus mutans*, thus exerting the anti-dental calculus and/or anti-cariogenic and/or anti-oral-malodor effect. The oral care composition may be a single or multiple phase composition.

In particular, the dentrifice of the present invention can be a paste, gel, or liquid formulation unless otherwise specified. The dentrifice composition may be in any desired form, such as deep striped, surface striped, multilayered, having the gel surrounding the paste, or any combination thereof. The dentrifice composition may be contained in a physically separated compartment of a dispenser and dispensed side-by-side. Dentifrice compositions are, for example, described in EP 0 617 608 B1.

Preferred dentifrice compositions are described in Examples 21 to 24 of WO 2008/074473 A2. In addition to the above described components, the dentifrice compositions of this invention can contain a variety of optional dentifrice ingredients some of which are described below. Optional ingredients include, for example, but are not limited to, adhesives, sudsing agents, flavouring agents, sweetening agents, additional antiplaque agents, additional abrasives, and colouring agents. These and other optional components are further described, for example, in U.S. Pat. Nos. 5,004,597, 4,885,155, 3,959,458 and 3,937,807.

For example, the toothpaste may include one or more surfactants, chelating agents, fluoride sources, teeth whitening actives and teeth color modifying substances, thickening agents, humectants, flavouring and sweetening agents, alkali metal bicarbonate salt, miscellaneous carriers and/or other active agents.

One of the preferred optional agents as used in accordance with the present invention is a surfactant, preferably one selected from the group consisting of sarcosinate surfactants, isethionate surfactants and taurate surfactants. Preferred for use herein are alkali metal or ammonium salts of these surfactants. Most preferred herein are the sodium and potassium salts of the following: lauroyl sarcosinate, myristoyl sarcosinate, palmitoyl sarcosinate, stearoyl sarcosinate and oleoyl sarcosinate.

Another preferred optional agent is a chelating agent such as tartaric acid and pharmaceutically-acceptable salts thereof, citric acid and alkali metal citrates and mixtures thereof. Chelating agents are able to complex calcium found in the cell walls of the bacteria. Chelating agents can also disrupt plaque by removing calcium from the calcium bridges, which help hold this biomass intact. However, as indicated above there is a preferred maximum concentration of such agents or such compositions which are intended for a particularly gentle treatment of teeth.

It is common to have an additional water-soluble fluoride compound present in dentifrices and other oral compositions in an amount sufficient to give a fluoride ion concentration in the. composition at 25° C., and/or when it is used of from about 0.0025% to about 5.0% by weight, preferably from about 0.005% to about 2.0% by weight, to provide additional anticaries effectiveness. A wide variety of fluoride ion-yielding materials can be employed as sources of soluble fluoride in the present compositions. Examples of suitable fluoride ion-yielding materials are found in U.S. Pat. Nos. 3,535,421 and 3,678,154. Representative fluoride ion sources include stannous fluoride, sodium fluoride, potassium fluoride, sodium monofluorophosphate and many others. Stannous fluoride and sodium fluoride are particularly preferred, as well as mixtures thereof.

The oral care compositions according to the present invention may also comprise teeth whitening actives, including bleaching or oxidizing agents such as peroxides, perborates, percarbonates, peroxyacids, persulfates, metal chlorites, and combinations thereof. Suitable peroxide compounds include hydrogen peroxide, urea peroxide, calcium peroxide, and mixtures thereof. A preferred percarbonate is sodium percarbonate. Other suitable whitening agents include potassium, ammonium, sodium and lithium persulfates and perborate mono- and tetrahydrates, and sodium pyrophosphate peroxyhydrate. Suitable metal chlorites include calcium chlorite, barium chlorite, magnesium chlorite, lithium chlorite, sodium chlorite, and potassium chlorite. The preferred chlorite is sodium chlorite. Additional whitening actives may be hypochlorite and chlorine dioxide.

In addition to bleaching agents as teeth whitening agents, teeth color modifying substances may be considered among the oral care actives useful in the present invention. These substances are suitable for modifying the color of the teeth to satisfy the consumer. These substances comprise particles that when applied on the tooth surface modify that surface in terms of absorption and, or reflection of light. Such particles provide an appearance benefit when a film containing such particles is applied over the surfaces of a tooth or teeth.

In preparing toothpaste or gels, it is necessary to add some thickening material to provide a desirable consistency of the composition, to provide desirable active release characteristics upon use, to provide shelf stability, and to provide stability of the composition, etc. Preferred thickening agents are carboxyvinyl polymers, carrageenan, hydroxyethyl cellulose, laponite and water soluble salts of cellulose ethers such as sodium carboxymethylcellulose and sodium carboxymethyl hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture.

Another optional component of the topical, oral carriers of the compositions of the subject invention is a humectant. The humectant serves to keep toothpaste compositions from hardening upon exposure to air, to give compositions a moist feel to the mouth, and, for particular humectants, to impart desirable sweetness of flavor to toothpaste compositions. The humectant, on a pure humectant basis, generally comprises from about 0% to about 70%, preferably from about 5% to about 25%, by weight of the compositions herein. Suitable humectants for use in compositions of the subject invention include edible polyhydric alcohols such as glycerin, sorbitol, xylitol, butylene glycol, polyethylene glycol, and propylene glycol, especially sorbitol and glycerin.

Flavoring and sweetening agents can also be added to the compositions. Suitable flavoring agents include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, thymol, linalool, cinnamaldehyde glycerol acetal known as CGA, and mixtures thereof. Flavouring agents are generally used in the compositions at levels of from about 0.001% to about 5%, by weight of the composition.

Sweetening agents which can be used include sucrose, glucose, saccharin, dextrose, levulose, lactose as described herein above, mannitol, sorbitol, fructose, maltose, xylitol, saccharin salts, thaumatin, aspartame, D-tryptophane, dihydrochalcones, acesulfame and cyclamate salts, especially sodium cyclamate and sodium saccharin, and mixtures thereof. An infant food composition preferably contains from about 0.1% to about 10% of these agents, preferably from about 0.1% to about 1%, by weight of the composition. Preferably, a pet food according to the present invention only has a low content of such sugars which can be metabolized by *mutans Streptococci* and preferably *Streptococcus mutans*, to avoid cariogenic activity of *mutans Streptococci*. Thus, the content of sucrose, cane sugar, caramel, corn syrup, corn molasses, glucose, fructose and sorbitol is preferably kept low, with a maximum content of 20 wt.-% of the total infant or pet food being preferred; a maximum content of 5 wt.-% is even more preferred, and a maximum content of 2 wt.-% being most preferred. Also preferably, the content of each of saccharin, dextrose, levulose, lactose, mannitol, maltose and xylitol is less than 20 wt.-%, more preferably less than 5 wt.-% and most preferably less than 2 wt.-%, with xylitol preferably being not contained in the pet food at all.

The oral care composition of the present invention may also include an alkali metal bicarbonate salt. Alkali metal bicarbonate salts are soluble in water and unless stabilized, tend to release carbon dioxide in an aqueous system. Sodium bicarbonate, also known as baking soda, is the preferred alkali metal bicarbonate salt. The present composition may contain from about 0.5% to about 30%, preferably from about 0.5% to about 15%, and most preferably from about 0.5% to about 5% of an alkali metal bicarbonate salt. Water employed in the preparation of commercially suitable oral compositions should preferably be of low ion content and free of organic impurities. Water generally comprises from about 10% to about 50%, and preferably from about 20% to about 40%, by weight of the aqueous toothpaste compositions herein. These amounts of water include the free water which is added plus that which is introduced with other materials, such as with sorbitol. Titanium dioxide may also be added to the present composition. Titanium dioxide is a white powder, which adds opacity to the compositions. Titanium dioxide generally comprises from about 0.25% to about 5% by weight of the dentifrice compositions.

The pH of the present compositions is preferably adjusted through the use of buffering agents. Buffering agents, as used herein, refer to agents that can be used to adjust the pH of the compositions to a range of about 4.5 to about 9.5, preferably 4.5 to 8.5. Buffering agents include monosodium phosphate, trisodium phosphate, sodium hydroxide, sodium carbonate, sodium acid pyrophosphate, citric acid, and sodium citrate. Buffering agents can be administered at a level of from about 0.5% to about 10%, by weight of the present compositions. The pH of dentifrice compositions is measured from a 3:1 aqueous slurry of dentifrice, e.g., 3 parts water to 1 part toothpaste.

Other optional agents that may be used in the present compositions include dimethicone copolyols selected from alkyl- and alkoxy-dimethicone copolyols, such as C12 to C20 alkyl dimethicone copolyols and mixtures thereof. Highly preferred is cetyl dimethicone copolyol marketed under the Trade Name Abil EM90. The dimethicone copolyol is generally present in a level of from about 0.01% to about 25%, preferably from about 0.1% to about 5%, more preferably from about 0.5% to about 1.5% by weight. The dimethicone copolyols aid in providing positive tooth feel benefits. Other useful carriers include biphasic dentifrice formulations such as those disclosed in U.S. Pat. Nos. 5,213,790, 5,145,666, 5,281,410, 4,849,213 and 4,528,180.

The present compositions may also include other active agents, such as antimicrobial agents. Included among such agents are water insoluble non-cationic antimicrobial agents such as halogenated diphenyl ethers, phenolic compounds including phenol and its homologs, mono and poly-alkyl and aromatic halophenols, resorcinol and its derivatives, bisphenolic compounds and halogenated salicylanilides, benzoic esters, and halogenated carbanilides. The water soluble antimicrobials include quaternary ammonium salts and bisbiquanide salts, among others. Triclosan monophosphate is an additional water soluble antimicrobial agent. The quaternary ammonium agents include those in which one or two of the substitutes on the quaternary nitrogen has a carbon chain length (typically alkyl group) from about 8 to about 20, typically from about 10 to about 18 carbon atoms while the remaining substitutes (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl) ammonium bromide, benzyl dimethylstearyl ammonium chloride, cetyl pyridinium chloride, quaternized 5-amino-1, 3-bis(2-ethyl-hexyl)-5-methyl hexa hydropyrimidine, benzalkonium chloride, benzethonium chloride and methyl benzethonium chloride are exemplary of typical quaternary ammonium antibacterial agents. Other compounds are bis [4-(R-amino)-1-pyridinium] alkanes as disclosed in U.S. Pat. No. 4,206,215. Other antimicrobials such as copper bisglycinate, copper glysinate, zinc citrate, and zinc lactate may also be included. Enzymes are another type of active that may be used in the present compositions. Useful enzymes include those that belong to the category of proteases, lytic enzymes, plaque matrix inhibitors and oxidases: Proteases include papain, pepsin, trypsin, ficin, bromelin; cell wall lytic enzymes include lysozyme; plaque matrix inhibitors include dextranses, mutanases; and oxidases include glucose oxidase, lactate oxidase, galactose oxidase, uric acid oxidase, peroxidases including horse radish peroxidase, myeloperoxidase, lactoperoxidase, chloroperoxidase. The oxidases also have whitening/cleaning activity, in addition to anti-microbial properties. Such agents are disclosed in U.S. Pat. No. 2,946,725 and in U.S. Pat. No. 4,051,234. Other antimicrobial agents include chlorhexidine, triclosan, triclosan monophosphate, and flavor oils such as thymol. Triclosan and other agents of this type are disclosed in U.S. Pat. Nos. 5,015,466 and 4,894,220. These agents, which provide anti-plaque benefits, may be present at levels of from about 0.01% to about 5.0%, by weight of the dentifrice composition.

The term "chewing gum" as defined herein means a confectionery composition which is suitable for chewing and which comprises any suitable amount of elastomer, known to the person skilled in the art, preferably an amount of 2% or greater, by weight of the composition. Suitable lozenge and chewing gum components are, for example, disclosed in U.S. Pat. Nos. 4,083,955, 6,770,264 or 6,270,781. Preferred lozenges are those described in Examples 19 and 20 of WO 2008/074473 A2. A preferred chewing gum composition is described in Example 25 of WO 2008/074473 A2.

Compositions of the present invention preferably comprise an elastomer, or mixture of several different elastomers. Elastomeric materials are generally known in the art but illustrative examples include styrene-butadiene rubber (SBR); synthetic gums; polyisobutylene and isobutylene-isoprene copolymers; natural gums; chicle; natural rubber; jelutong; balata; guttapercha; lechi caspi; sorva; and mixtures thereof. Compositions as used in accordance with the present invention preferably comprise from about 2% to about 30%, more preferably from about 5% to about 25%, by weight, of elastomer. These levels are determined by the desired final texture of the chewing gum since when the total level of elastomer is below about 2% the base composition lacks elasticity, chewing texture, and cohesiveness whereas at levels above about 30% the formulation is hard, rubbery and maintains a tight chew. Elastomer solvents are also preferably present in compositions as used in accordance with the present invention since they aid softening of the elastomer component. Preferred examples of elastomer solvents for use herein include the pentaerythritol ester of partially hydrogenated wood rosin, pentaerythritol ester of wood rosin, glycerol ester of partially dimerized rosin, glycerol ester of polymerised rosin, glycerol ester of tall oil, wood or gum rosin, glycerol ester of partially hydrogenated rosin, methyl ester of partially hydrogenated rosin, and mixtures thereof. Compositions as used in accordance with the present invention preferably comprise from about 2% to about 50%, more preferably from about 10% to about 35%, by weight, of elastomer solvent.

Lozenges of this invention can be prepared, for example, by art-recognized techniques for forming compressed tablets where the disaccharide is dispersed on a compressible solid carrier, optionally combined with any appropriate tableting aids such as a lubricant (e.g., magnesium-stearate) and is compressed into tablets. The solid carrier component for such tableting formulations can be a saliva-soluble solid, such as a cold water-soluble starch or a monosaccharide, so that the lozenge will readily dissolve in the mouth to release the contained disaccharide acid in saliva solution for contact with and absorption by the oral/pharyngeal mucosa when the lozenge is held in the mouth. The pH of the above-described formulations can range from about 4 to about 8.5. Lozenges in accordance with the present invention can also be prepared utilizing other art-recognized solid unitary dosage formulation techniques.

A mouth wash or mouth rinse of the present invention could contain EtOH or could be EtOH-free, and could contain other active ingredients, as e.g. antimicrobials such as Chlorhexidin. A preferred mouth wash or mouth rinse of the present invention could be as follows:

A Olium menthae 1.2 parts
   Tinctura Arnicae 3.0 parts
   Tinctura Myrrhae 3.0 parts
   Tween 5.0 parts
B Spiritus 90% 50.0 parts
C Sodium Benzoate 0.2 parts
Sweetening agent (e.g. aspartame) 0.02 parts
Aqua destilata ad 100.0

A is to be well mixed, B is added under stirring and C is added subsequently. The resulting clear liquid is to be filtered within 48 hours after preparation. Another preferred mouth wash is described in Example 26 of WO 2008074473 A2.

Regardless of the dosage form, liquid or solid, in one preferred embodiment of the present invention the dosage form is held in the consumer's mouth, preferably the pet animal's mouth, for a period of time to promote contact of the microorganism or analog or fragment of a above mentioned microorganism belonging to the group of lactic acid bacteria with the patient's oral cavity.

The terms "dental floss" and "dental tape" as used herein refer to a material to dislodge and remove decomposing food material that accumulated at interproximal and subgingival surfaces and to dislodge and remove bacteria, plaque and/or calculus that accumulated in the oral cavity. The dental floss or dental tape may further contain, in addition to the microorganisms according to the present invention as described herein, cleaners, abrasives, tartar control ingredients, whiteners, surfactants and/or active ingredients like fluorides, antimicrobials, chemotherapeutic agents or antibiotics. Further additional agents are antiplaque agents, flavouring agents and colouring agents. The dental floss or dental tape may be in any suitable form, known to the person skilled in the art, for example, in the form of PTFE (Teflon) dental flosses as described, for instance, in U.S. Pat. Nos. 3,664,915, 3,953,566, 3,962,153, 4,096,227, 4,187,390, 4,256,806, 4,385,093, 4,478,665, 4,776,358, 5,033,488, 5,209,251, 5,220,932, 5,518,012, 5,718,251, 5,765,576 or U.S. Pat. No. 5,911,228, in the form of monofilament interproximal devices as described, for instance, in U.S. Pat. Nos. 3,800,812, 4,974,615, 5,760,117, 5,433,226, 5,479,952, 5,503,842, 5,755,243, 5,884,639, 6,003,525 or U.S. Pat. No. 6,027,592, or in the form of biocomponent tapes. Preferably, the dental floss or dental tape may be in the form of an elastomeric coated monofilament as described, for instance, in US 20050226820 or in the form of an oriented thermoplastic based dental tape as described, for instance, in US 20020144704.

The oral care cosmetic compositions as described herein, particularly anti-dental calculus compositions, anti-caries compositions and anti-oral malodor compositions, may be used in the ambit of human oral administration as well as in the ambit of veterinary oral administration, preferably for non-human mammals, more preferably for pets. If the composition is used in the ambit of veterinary oral administration, the composition may contain further ingredients suitable for such an administration, as known by a person skilled in the art.

A pharmaceutical composition according to the present invention preferably further comprises a pharmaceutical acceptable carrier or excipient.

Pharmaceutical compositions comprise a therapeutically effective amount the above mentioned microorganism or fragment thereof and can be formulated in various forms, e.g. in solid, liquid, powder, aqueous, lyophilized form.

The pharmaceutical composition may be administered with a pharmaceutically acceptable carrier to a patient, preferably a human being or an animal, and most preferably a child or pet animal. The term "pharmaceutically acceptable" means approved by a regulatory agency or other generally recognized pharmacopoeia for use in animals, and more particularly in humans. A preferred pharmaceutical composition as used in accordance with the present invention does not contain lactose in a range between 1% (w/w) and 6% (w/w). It is also preferred that the pharmaceutical composition contains not more than 1% (w/w) lactose, e.g. it contains less than 1%, preferably less than 0.9% (w/w), 0.8% (w/w) lactose, etc. or that the pharmaceutical composition contains more than 6%, 7%, 8% etc. (w/w) lactose. Alternatively, but also preferred is that the pharmaceutical composition does not contain lactose.

The term "carrier" refers to a diluent, adjuvant, excipient, or vehicle with which the therapeutic is administered. Such a carrier is pharmaceutically acceptable, i.e. is non-toxic to a recipient at the dosage and concentration employed. It is preferably isotonic, hypotonic or weakly hypertonic and has a relatively low ionic strength, such as provided by a sucrose solution. Such pharmaceutical carriers can be sterile liquids, such as water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. Suitable pharmaceutical excipients include starch, glucose, sucrose, gelatin, malt, rice, flour, chalk, silica gel, sodium stearate, glycerol monostearate, talc, sodium ion, dried skimmed milk, glycerol, propylene, glycol, water, ethanol and the like. The excipient may contain lactose as described herein above, most preferably it is lactose-free. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard carriers such as pharmaceutical grades of maltodextrin, mannitol, starch, magnesium stearate, sodium saccharine, cellulose, magnesium carbonate, etc. Examples of suitable pharmaceutical carriers are described in "Remington's Pharmaceutical Sciences" by E. W. Martin. Skimmed milk, skimmed milk powder, non-milk or non-lactose containing products may also be employed. The skimmed milk powder is conventionally suspended in phosphate buffered saline (PBS), autoclaved or filtered to eradicate proteinaceous and living contaminants, then freeze dried heat dried, vacuum dried, or lyophilized. Some other examples of substances which can serve as pharmaceutical carriers are sugars, such as glucose and sucrose; starches such as corn starch and potato starch; cellulose and its derivatives such as sodium carboxymethylcellulose, ethylcellulose and cellulose acetates; powdered tragacanth; malt; gelatin; talc; stearic acids; magnesium stearate; calcium sulfate; calcium carbonate; vegetable oils, such as peanut oils, cotton seed oil, sesame oil, olive oil, corn oil and oil of theobroma; polyols such as propylene glycol, glycerine, sorbitol, manitol, and polyethylene glycol; agar; alginic acids; pyrogen-free water; isotonic saline; cranberry, extracts and phosphate buffer solution; skim milk powder; as well as other non-toxic compatible substances used in pharmaceutical formulations such as Vitamin C, estrogen and echinacea, for example. Wetting agents and lubricants such as sodium lauryl sulfate, as well as colouring agents, flavouring agents, lubricants, excipients, tabletting agents, stabilizers, anti-oxidants and preservatives, can also be present.

Preferably, the oral formulation contains lactose as described herein and is most preferably lactose-free. Various carriers and/or excipients suitable for oral administration which are well known in the art may be used for the purpose of this invention. The non-cariogenic composition may, if desired, further contain various known additives such as, for example, preservatives, hardening agents, lubricants, emulsifiers, stabilizers, essence and the like. Such compositions will contain a therapeutically effective amount of the aforementioned compounds, preferably in purified form, together with a suitable amount of carrier so as to provide the form for proper administration to the patient. The formulation should suit the mode of administration.

A preferred composition of the present invention does not contain lactose in a range between 1% (w/w) and 6% (w/w). It is also preferred that the composition contains not more than 1% (w/w) lactose, e.g. it contains less than 1%, preferably less than 0.9% (w/w), 0.8% (w/w) lactose, etc. or that the composition contains more than 6%, 7%, 8% etc. (w/w) lactose. Alternatively, but also preferred is that the composition does not contain lactose.

In a further aspect, a composition of the present invention may be produced by comprising the steps of formulating a binder microorganism fragment thereof with a cosmetically, orally or pharmaceutical acceptable carrier or excipient. Preferably, this microorganism is a deposited microorganism as described herein above or a mutant, derivative, analog or fragment thereof. A preferred composition in accordance with the present invention does not contain lactose in a range between 1% (w/w) and 6% (w/w). It is also preferred that the composition contains not more than 1% (w/w) lactose, e.g. it contains less than 1%, preferably less than 0.9% (w/w), 0.8% (w/w) lactose, etc., or that the composition contains more than 6%, 7%, 8% etc. (w/w) lactose. Alternatively, but also preferred is that the composition does not contain lactose.

The composition of the present invention, preferably a food or feed composition including pharmaceutical compositions, comprises a binder microorganism as described above, potentially in a thermally inactivated or lyphilized form, in an amount of $10^2$ to $10^{12}$ cells, preferably $10^3$ to $10^8$ cells per mg in a solid form of the composition. In case of a liquid form of the composition, the amount of the microorganisms is $10^2$ to $10^{13}$ cells per ml. However, for specific compositions the amount of the microorganism may be different as is described herein.

Preferably, the concentration of binder microorganisms in the composition of the present invention is 0.01 wt.-% to 10 wt.-%, relative to the total mass of the composition. Even more preferably, the concentration of binder microorganisms in the composition of the present invention is 0.025 wt.-% to 2 wt.-%. As described above, when fragments are used instead of binder cells, then the concentration of fragments is chosen to be the same as the peptidoglycan content of binder cells.

In accordance with the present invention, the term food encompasses all eatable and drinkable foods and drinks. Accordingly, the microorganism or fragment thereof may be included in a food or drink. These are, for example, gum, spray, beverage, candies, infant formula, ice cream, frozen dessert, sweet salad dressing, milk preparations, cheese, quark, lactose-free yogurt, acidified milk, coffee cream or whipped cream and the like.

Milk-based products are envisaged within the framework of the invention. Milk is however understood to mean that of animal origin, such as cow, goat, sheep, buffalo, zebra, horse, donkey, or camel, and the like. The milk may be in the native state, a reconstituted milk, a skimmed milk or a milk supplemented with compounds necessary for the growth of the bacteria or for the subsequent processing of fermented milk, such as fat, proteins of a yeast extract, peptone and/or a surfactant, for example. The term milk also applies to what is commonly called vegetable milk, that is to say extracts of plant material which have been treated or otherwise, such as leguminous plants (soya bean, chick pea, lentil and the like) or oilseeds (colza, soya bean, sesame, cotton and the like), which extract contains proteins in solution or in colloidal suspension, which are coagulable by chemical action, by acid fermentation and/or by heat. Finally, the word milk also denotes mixtures of animal milks and of vegetable milks.

Where the binder microorganism of this invention or fragment thereof are added to yogurt and the like having similar contents, it is sufficient to add the microorganism of this invention at a concentration of about $10^5$-$10^7$ cells/ml, or the equivalent amount of fragment thereof. In such a case, it is possible to completely prevent or inhibit formation of a biofilm by mutans Streptococci, preferably by *Streptococcus mutans*, and thus to prevent or slow the development of dental calculus, oral malodour or dental caries induced by cariogenic strains, without significant side effect upon the quality of the drink per se.

Such food drink or feed can be produced by a general method for producing foods and drinks or feeds, including adding the active ingredient to a raw or cooked material of the food, drink or feed. The food, drink or feed in accordance with the present invention can be molded and granulated in the same manner as generally used for foods, drinks or feeds. The molding and granulating method includes granulation methods such as fluid layer granulation, agitation granulation, extrusion granulation, rolling granulation, gas stream granulation, compaction molding granulation, cracking granulation, spray granulation, and injection granulation, coating methods such as pan coating, fluid layer coating, and dry coating, puff dry, excess steam method, foam mat method, expansion methods such as microwave incubation method, and extrusion methods with extrusion granulation machines and extruders.

The food, drink or feed of the present invention includes any food, drink or feed which comprises the binder microorganism of the invention or fragment thereof as active ingredient. The active ingredient in the food, drink or feed is not specifically limited to any concentration as long as the resulting food, drink or feed can exert its activity of specifically binding to *mutans Streptococci*. The concentration of the active ingredient is preferably 0.001 to 100% by weight, more preferably 0.01 to 100% by weight and most preferably 0.1 to 100% by weight of the food, drink or feed comprising such active ingredient or with respect to the cell number those described herein.

Specific foods or drinks, to which the active ingredient is added, include, for example, juices, refreshing drinks, soups, teas, sour milk beverages, dairy products such as fermented milks, ices, butter, cheese, processed milk and skim milk, meat products such as ham, sausage, and hamburger, fish meat cake products, egg products such as seasoned egg rolls and egg curd, confectioneries such as cookie, jelly, snacks, and chewing gum, breads, noodles, pickles, smoked products, dried fishes and seasonings. The form of the food or drink includes, for example, powder foods, sheet-like foods, bottled foods, canned foods, retort foods, capsule foods, tablet foods and fluid foods.

The food or drink according to the invention to be ingested by infants, i.e. comprising the binder microorganism of fragment thereof with an activity to specifically bind to *mutans Streptococci*, is preferably a nutritious composition for infants. Such nutritious composition for infants includes modified milk prepared for infants, protein-decomposed milk, specific nutritionally modified milk or baby foods and foods prepared for toddlers. The form of the nutritious composition for infants includes but is not specifically limited to powder milks dried and pulverized and baby foods and also include general foods such as ice cream, fermented milk, and jelly for infantile ingestion.

The nutritious composition for infants, and also the nutritious food or feed composition for animals and particularly pet animals, in accordance with the present invention is principally composed of protein, lipid, saccharide, vitamins and/or minerals. In the nutritious composition, the active ingredient is blended with these components. The protein includes milk proteins such as skim milk, casein, cheese whey, whey protein concentrate and whey protein isolates and their fractions such as alpha s-casein, beta-casein, alpha-lactoalbumin and beta-lactoglobulin. Further, egg protein such as egg yolk protein, egg white protein, and ovalbumin, or soybean protein such as defatted soybean protein, separated soybean protein, and concentrated soybean protein can be used. Other than these, proteins such as wheat gluten, fish meat protein, cattle meat protein and collagen may also be used satisfactorily. Further, fractions of these proteins, peptides from the acid or enzyme treatment thereof, or free amino acids maybe used satisfactorily as well. The free amino acids can serve as nitrogen sources and can additionally be used to give specific physiological actions. Such free amino acids include, for example, taurine, arginine, cysteine, cystine and glutamine. For dogs, these include arginine, methionine, histidine, phenylalanine, isoleucine, threonine, leucine, tryptophan, lysine and valine. For cats, taurine is also essential. The lipid includes animal fats and oils such as milk fat, lard, beef fat and fish oil, vegetable oils such as soybean oil, rapeseed oil, corn oil, coconut oil, palm oil, palm kernel oil, safflower oil, perilla oil, linseed oil, evening primrose oil, medium chain fatty acid triglyceride, and cotton seed oil, bacterially generated fats and oils, and fractionated oils thereof, hydrogenated oils thereof, and ester exchange oils thereof. The amount of lipid to be blended varies depending on the use.

Further preferred ingredients of food and feed, particularly pet feed, are omega-6 fatty acids and omega-3 fatty acids. Particularly preferred are linoleic acid, preferably in the form of corn, soy, canola, safflower and sunflower oil, whole grains and/or body fat of poultry; arachidonic acid, preferably in the form of body fat of poultry, lean meat, egg yolks and/or fish oil; gamma linolenic acid, preferably in the form of black currant seed oil, borage oil and/or evening primrose oil; dihomogamma linolenic acid, preferably in the form of spleen, kidney, adrenals and/or metabolized from gla; alpha linolenic acid, preferably in the form of flaxseed oil, canola, soy, and/or walnut oils; eicosapentaenoic acid, preferably in the form of cold water fish and their oil; docosahexaenoic acid, preferably in the form of cold water fish and their oil.

The saccharide includes, for example, one or more of starch, soluble polysaccharides, dextrin, monosaccharides such as sucrose, lactose as described herein, maltose, glucose, and fructose and other oligosaccharides. Preferred saccharides include glucose, fructose, honey, galactose, lactose, sucrose, maltose, dextrins, glycogen and starch. However, as described above the maximum content of glucose, fructose, honey, galactose, lactose, sucrose and maltose preferably is 20 wt.-% of the total composition, more preferably 5 wt.-% of the total composition, and most preferably 2 wt.-% of the total composition. Even more preferably, the aforementioned maximum content of 20 wt.-%, more preferably 5 wt.-% and most preferably 2 wt.-% applies to the total of all substances of the group of cane sugar, caramel, corn molasses, corn syrup, dextrose, fructose, galactose, glucose, honey, lactose, levulose, maltose, mannitol, saccharin, sorbitol, sucrose and xylitol, and most preferably to the total of mono- and disaccharides.

Also preferred are dietary fiber preferably selected form cellulose, hemicellulose, pectin, plant gums and mucilages, beet pulp, guar gum, gum arabic, xanthan gum and locust bean gum. The total amount of such saccharide is preferably 40 to 80% by weight to the total solid in the nutritious composition. Further, artificial sweeteners such as aspartame may be used satisfactorily. The amount of an artificial sweetener is appropriately 0.05 to 1.0% by weight per the total solid in the nutritious composition.

The vitamins include, but are not limited to, lycopene as an essential component and additionally include, for example, vitamins such as vitamin A, vitamin B group, vitamins C, D, and E and vitamin K group, folic acid, pantothenic acid, nicotinamide, carnitine, choline, inositol and biotin as long as such vitamins can be administered to infants or pet animals. Such vitamins are preferably from 10 mg to 5 g by weight per the total solid in the nutritious composition for infants. Preferred vitamins for nutrious compositions for infants and/or animals, preferably pet animals, include:

Vitamin A (Retinol), and/or beta carotene as precursor. The vitamin is preferably present in the form of liver, fish liver oil, carrots, green leafy vegetables, egg yolks and/or yellow fruits or in form of synthetic forms of Vitamin A and/or beta-carotene.

Vitamin D (Calciferol). The vitamin is preferably present in the form of halibut and/or cod liver oil, saltwater fish, cheese, yogurt and/or eggs or in form of synthetic forms of Vitamin D.

Vitamin E (Tocopherol). The vitamin is preferably present in the form of germ, corn, nuts, seeds, spinach and/or other green leafy vegetables, asparagus, vegetable oils or in form of synthetic forms of Vitamin E.

Vitamin K (Naphthoquinone). The vitamin is preferably present in the form of cabbage, cauliflower, spinach and/or other green leafy vegetables, cereals, soybeans, and/or other vegetables or in form of synthetic forms of Vitamin K. Preferably, the food or feed does not comprise menadione.

Vitamin B1 (Thiamine). The vitamin is preferably present in the form of wheat germ, rice and/or other whole grains, lean meats (especially pork), liver, fish, yeast, dried beans, peas and/or soybeans or in form of synthetic forms of Vitamin B1.

Vitamin B2 (Riboflavin). The vitamin is preferably present in the form of lean meats, liver, fish, eggs, yeast, cheese, legumes, nuts and/or green leafy vegetables or in form of synthetic forms of Vitamin B2.

Vitamin B3 (Niacin). The vitamin is preferably present in the form of liver, lean meat, poultry, fish, nuts, yeast, legumes, asparagus, seeds and/or green leafy vegetables or in form of synthetic forms of Vitamin B3.

Vitamin B5 (Pantothenic Acid). The vitamin is preferably present in the form of eggs, fish, lean beef, legumes, yeast, broccoli and/or other vegetables in the cabbage family, white and/or sweet potatoes or in form of synthetic forms of Vitamin B5.

Vitamin B6 (Pyridoxine). The vitamin is preferably present in the form of meat, fish, eggs, bananas and/or whole grains or in form of synthetic forms of Vitamin B6.

Vitamin B8 (Biotin). The vitamin is preferably present in the form of raw egg yolk, liver and/or vegetables or in form of synthetic forms of Vitamin B8.

Vitamin B9 (Folic Acid, Folate). The vitamin is preferably present in the form of carrots, yeast, liver, egg yolks, melon, apricots, pumpkin, beans, rye, whole wheat and/or green leafy vegetables or in form of synthetic forms of Vitamin B9.

Vitamin B12 (Cobalamin). The vitamin is preferably present in the form of fish, liver, meat, poultry, eggs and/or cheese or in form of synthetic forms of Vitamin B12.

Vitamin C (Ascorbic Acid). The vitamin is preferably present in the form of citrus fruit juice or pulp, berries, tomatoes, cauliflower, potatoes, green leafy vegetables and/or green peppers or in form of synthetic forms of Vitamin C. Supplementation in an appropriate form, preferably as calcium ascorbate, is preferred due to its beneficial effects on dogs suffering from chronic joint and musculoskeletal disorders. In puppies it helps to prevent the development of such disorders.

Further, the minerals include calcium, magnesium, potassium, sodium, iron, copper, zinc, phosphorus, chlorine, manganese, selenium and iodine. Such minerals are preferably from 1 mg to 5 g by weight per the total solid in the nutritious composition for infants.

Other than those components described above, the nutritious composition for infants, and also the food or feed composition for animals, preferably pet animals, as used in accordance with the present invention may be blended with any component desirably blended in nutritious compositions, for example, dietary fiber, nucleotides, nucleic acids, flavors, and colorants.

The food or drink as used in accordance with the present invention can be used as a health food or drink or a functional food or drink to prevent and/or treat caries and/or to prevent or treat oral malodour and/or to prevent or treat dental calculus.

When the food or drink according to the present invention is ingested, the amount to be ingested is not specifically limited. The amount to be ingested is generally 0.1 to 50 g, preferably 0.5 g to 20 g daily, based on the total amount of active ingredient.

The food or drink is continuously ingested at this amount for a period from a single day up to 5 years, preferably from 2 weeks to one year. Herein, the amount ingested can be adjusted to an appropriate range depending on the severity of the symptom of the individual ingesting the food or drink, the age and body weight thereof, and the like.

The composition of the present invention may comprise, further to the binder microorganism or fragment thereof, cereals, brans, oil-seed meals, animal-derived raw feed materials, other raw feed materials and purified products. The cereals can include, mile, wheat, barley, oats, rye, brown rice, buckwheat, fox-tail millet, Chinese millet, Deccan grass, corn, and soybean. The brans can include, rice bran, defatted rice bran, bran, lowest-grade flour, wheat germ, barley bran, screening pellet, corn bran, and corn germ. The oil-seed meals include, for example, soybean meal, soybean powder, linseed meal, cotton-seed meal, peanut meal, safflower meal, coconut meal, palm meal, sesame meal, sunflower meal, rapeseed meal, kapok seed meal and mustard meal. The animal-derived raw feed materials include, for example, fish powders, import meal, whole meal, and coast meal, fish soluble, meat powder, meat and bone powder, blood powder, decomposed hair, bone powder, byproducts from butchery, feather meal, silkworm pupa, skim milk, casein, dry whey and krill. Other raw feed materials include, for example, plant stems and leaves such as alfalfa, hey cube, alfalfa leaf meal, and locust leaf powder, byproducts from corn processing industries, such as corn gluten meal, corn gluten feed and corn steep liquor, starch, sugar, yeast, byproducts from fermentation industry such as beer residue, malt root, liquor residue and soy sauce residue, and agricultural byproducts such as citrus processed residue, soybean curd residue, coffee residue, and cocoa residue, cassava, horse bean, guar meal, seaweed, spirulina and chlorella. The purified products include, for example, proteins such as casein and albumin, amino acids, starch, cellulose, saccharides such as sucrose and glucose, minerals and vitamins.

The composition of the present invention may further comprise one or more additives. Such additive for foods can be produced by a general method for producing additives for foods, drinks or feeds. If necessary, additives for general use in foods, drinks or feeds, for example, additives described in Food Additive Handbook (The Japan Food Additives Association; issued on Jan. 6, 1997) may be added satisfactorily, including sweeteners, colorants, preservatives, thickeners and stabilizers, antioxidants, color fixing agents, bleaches, antiseptics, gum base, bitters, enzymes, brightening agents, acidifier, seasonings, emulsifiers, enhancers, agents for manufacture, flavors, and spice extracts. Further, conventional saccharides, starch, inorganic materials, plant powders, excipients, disintegrators, lubricants, binders, surfactants, and plasticizers mentioned previously for pharmaceutical tablets may be added satisfactorily.

The sweeteners include Brazzein; Curculin; Erythritol; Glycyrrhizin; Glycerol, E422; Hydrogenated starch hydrolysates; Inulin; Isomalt, E953; Lactitol, E966; Luo han guo; Mabinlin; Maltitol, E965; Malto-oligosaccharide; Mannitol, E421; Miraculin; Monatin; Monellin; Pentadin; Sorbitol, E420; Stevia extracts or steviol glycosides, particularly Stevioside, Rebaudioside A, Rebaudioside C, Dulcoside A, Rubusoside, Steviolbioside H and Rebaudioside B; Tagatose; Thaumatin, E957; Xylitol, E967; Acesulfame potassium, E950; Alitame; Aspartame, E951; Salt of aspartame-acesulfame, E962; Cyclamate, E952; Dulcin; Glucin; Neohesperidin dihydrochalcone, E959; Neotame; P-4000; Saccharin, E954; Sucralose, E955; licorice; xylose and rakanka (*Momordica grosvenori* fruit).

The colorants include carotenoid and turmeric oleoresin, flavonold, caramel color, spirulina color, chlorophyll, purple sweet potato color, purple yarn color, perilla color, and blueberry color.

The preservatives include, for example, sodium sulfite, benzoates, benzoin extract, sorbates, and propionates.

The thickeners and stabilizers include, for example, gums such as gum arable and xanthan gum, alginates, chitin, chitosan, aloe extract, guar gum, hydroxypropyl cellulose, sodium casein, corn starch, carboxymethyl cellulose, gelatin, agar, dextrin, methyl cellulose, polyvinyl alcohol, microfiber cellulose, microcrystalline cellulose, seaweed cellulose, sodium polyacrylate, sodium polyphosphate, carrageenan or yeast cell wall.

The anti-oxidants include, for example, vitamin C group, sodium ethylenediaminetetraacetate, calcium ethylenediaminetetraacetate, erythorbic acid, oryzanol, catechin, quercetin, clove extract, enzyme-treated rutin, apple extract, sesame seed extract, dibutylhydroxytoluene, fennel extract, horseradish extract, water celery extract, tea extract, tocopherols, rapeseed extract, coffee bean extract, sunflower seed extract, ferulio acid, butylhydroxyanisole, blueberry leaf extract, propolis extract, pepper extract, garden balsam extract, gallic acid, eucalyptus extract, and rosemary extract.

The color fixing agents include, for example, sodium nitrite. The bleaches include, for example, sodium sulfite.

The antiseptics include, for example, o-phenyl phenol. The gum base includes, for example, acetylricinoleate methyl, urushi wax, ester gum, elemi resin, urucury wax, kaurigum, carnaubawax, glycerin fatty acid ester, spermaceti wax, copaibabalsam, copal resin, rubber, rice bran wax, cane wax, shellac, jelutong, sucrose fatty acid ester, depolymerized natural rubber, paraffin wax, fir balsam, propylene glycol fatty acid ester, powdered pulp, powdered rice hulls, jojoba oil, polyisobutylene, polybutene, microcrystalline wax, mastic gum, bees wax and calcium phosphate. The bitters include, for example, iso-alpha-bitter acid, caffeine, kawaratake (*Coriolus versieolor*) extract, redbark cinchona extract, Phellodendron bark extract, gentian root extract, spice extracts, enzymatically modified naringin, Jamaica cassia extract, theabromine, naringin, cassia extract, absinth extract, isodonis extract, olive tea, bitter orange (*Citrus aurantium*) extract, hop extract and wormwood extract. The enzymes include, for example, amylase, trypsin or rennet. The brightening agents include, for example, urushi wax and japan wax. The acidifier include, for example, adipic acid, itacania acid, citric acids, succinic acids, sodium acetate, tartaric acids, carbon dioxide, lactic acid, phytic acid, fumario acid, malic acid and phosphoric acid. The seasonings include, for example, amino acids such as asparagine, aspartic acid, glutamic acid, glutamine, alanine, isoleucine, glycine, serine, cystine, tyrosine, leucine, and praline, nucleic acids such as sodium inosinate, sodium uridinate, sodium guanylate, sodium cytidylate, calcium ribonucleotide and sodium ribonucleotide, organic acids such as citric acid and succinic acid, potassium chloride, sodium chloride-decreased brine, crude potassium chloride, whey salt, thpotassium phosphate, dipotassium hydrogen phosphate, potassium dihydrogen phosphate, disodium hydrogen phosphate, sodium dihydrogen phosphate, trisodium phosphate and chlorella extract.

The enhancers include, for example, zinc salts, vitamin C group, various amino acids, 5-adenylic acid, iron chloride, hesperidin, various calcined calcium, various non-calcined calcium, dibenzoylthiamine, calcium hydroxide, calcium carbonate, thiamine' hydrochloride salt, Dunallella. Oarotene, tocopherol, nicotinic acid, carrot carotene, palm oil carotene, calcium pantothenate, vitamin A, hydroxyproline, calcium dihydrogen pyrophosphate, ferrous pyrophosphate, ferric pyrophosphate, ferritin, heme iron, menaquinone, folic acid and riboflavine.

The agents for manufacture include, for example, processing auxiliaries such as acetone and ion exchange resin.

The flavors include, for example, vanilla essence and the spice extracts include, for example, capsicum extract.

These various additives can be added to the active ingredient, taking into consideration the mode of administration, in accordance with the present invention.

It is envisaged that the composition of the present invention, preferably the food or feed composition or pharmaceutical composition, comprises the above mentioned binder microorganism belonging to the group of lactic acid bacteria in the form of a probiotic microorganism. Namely, in addition to the probiotic effect, the above mentioned probiotic microorganism belonging to the group of lactic acid bacteria is useful for treating and/or preventing biofilm formation caused by *mutans Streptococci*. The amount of said probiotic microorganism is high enough to significantly positively modify the condition to be treated, preferably caries, dental calculus and/or oral malodour, but low enough to avoid serious side effects (at a reasonable benefit/risk ratio), within the scope of sound medical judgment. An effective amount of said probiotic microorganism will vary with the particular goal to be achieved, the age and physical condition of the patient being treated, the severity of the underlying disease, the duration of treatment, the nature of concurrent therapy and the specific microorganism employed. The effective amount of said probiotic microorganism will thus be the minimum amount which will provide the desired specific binding to *mutans Streptococci*. The presence of, for example, $1 \times 10^9$ bacteria, as viable or non-viable whole cells, in 0.05 ml solution of phosphate buffered saline solution, or in 0.05 ml of suspension of agar, or the dry weight equivalent of cell wall fragments, is effective when administered in quantities of from about 0.05 ml to about 20 ml. A decided practical advantage is that the probiotic organism may be administered in a convenient manner such as by the oral route. Depending on the route of administration, the active ingredients which comprise said probiotic organisms may be required to be coated in a material to protect said organisms from the action of enzymes, acids and other natural conditions which may inactivate said organisms. In order to administer probiotic organisms by other than parenteral administration, they should be coated by, or administered with, a material to prevent inactivation. For example, probiotic organisms may be coadministered with enzyme inhibitors or in liposomes. Enzyme inhibitors include pancreatic trypsin inhibitor, diisopropylfluorophosphate (DFP) and trasylol. Liposomes include water-in-oil-in-water P40 emulsions as well as conventional and specifically designed liposomes which transport lactobacilli or their by-products to the urogenital surface. Dispersions can also be prepared, for example, in glycerol, liquid polyethylene glycols, and mixtures thereof, and in oils. Generally, dispersions are prepared by incorporating the various sterilized probiotic organisms into a sterile vehicle which contains the basic dispersion medium and the required other ingredients from those enumerated above. In the case of sterile powders for the preparation of sterile injectable solutions, the preferred methods of preparation are vacuum-drying and the freeze-drying technique which yield a powder of the active ingredient plus any additional desired ingredient from previously sterile-filtered solution thereof. Additional preferred methods of preparation include but are not limited to lyophilization and heat-drying.

The composition of the present invention also encompasses products intended to be administered orally, or buccal, which comprise an acceptable pharmaceutical carrier as described herein to which, or onto which, cells of the above mentioned microorganism belonging to the group of lactic acid bacteria is added in fresh, concentrated or dried form, for example. These products may be provided in the form of an ingestible suspension, a gel, a diffuser, a capsule, a hard gelatin capsule, a syrup, or in any other galenic form known to persons skilled in the art.

When the probiotic organisms are suitably protected as described above, the active compound may be orally administered, for example, with an inert diluent or with an assimilable edible carrier, or it may be enclosed in hard or soft shell gelatin capsule, or it may be compressed into tablets designed to pass through the stomach (i.e., enteric coated), or it may be incorporated directly with the food of the diet. For oral therapeutic administration, the probiotic organisms may be incorporated with excipients and used in the form of ingestible tablets, buccal tablets, troches, capsules, elixirs, suspensions, syrups, wafers, and the like. Compositions or preparations according to the present invention are prepared so that an oral dosage unit form contains, for example, about $1 \times 10^9$ viable or non-viable cells per ml, e.g. lactobacilli per ml. The probiotic organism is compounded for convenient and effective administration in effective amounts with a suitable pharmaceutically or food acceptable carrier in dosage unit form as hereinbefore disclosed. A unit dosage form can, for example, contain the principal active compound in an amount approximating $10^9$ viable or non-viable, e.g., lactobacilli, per ml. In the case of compositions containing supplementary ingredients such as prebiotics, the dosages are determined by reference to the usual dose and manner of administration of the said ingredients.

Preferred ingredients in the food and feed composition according to the present invention are alfalfa, alfalfa concentrate powder, alfalfa dehydrated meal, alfalfa nutrient concentrate, alpha-lipoic acid, animal digest, animal fat, argenine, artificial flavor, ascorbic acid, asparagus, *Bacillus subtilis*, bacon, bacon flavors, barley, barley grass, barley malt flour, basil, beans, beef, beef & bone meal, beef broth, beef by-products, beef flavor, beef liver, beef meal, beef tallow, beet pulp, beet pulp (sugar removed), beets, beta carotene, BHA, *Bifidobacterium longum, Bifidobacterium pseudolongum, Bifidobacterium thermophilum*, biotin, blue 2, blue 2 and other color, blueberries, bone meal, borage oil, brewers dried yeast, brewers yeast, brewers yeast extract (*Saccharomyces cerevisiae* fermentation solubles), brewer's rice, broccoli, brown rice, brown rice flour, calcium, calcium ascorbate, calcium carbonate, calcium chloride, calcium iodate, calcium pantothenate, calcium phosphate, calcium propionate, calcium sulfate, cane molasses, canola meal, canola oil, canthaxanthin, caramel, caramel color, carmine, carrageenan, carrageenan gum, carrot powder, carrots, casein, catfish, catfish meal, celery, cellulose, cellulose powder, cheese powder, chelated cobalt, chelated copper, chelated iron, chelated potassium, chicken, chicken broth, chicken by products organs only, Chicken by-product, chicken by-product meal, chicken by-products organ meat only, chicken cartilage natural, chicken fat, chicken fat naturally, chicken flavors, chicken giblets, chicken liver, chicken liver digest, chicken liver flavor, chicken meal, chicken natural, chicken stock, chicory extract, choline chloride, chondroitine sulfate, cinnamon, citric acid, citric acid and rosemary, citric acid and rosemary extract, citrus pectin, clove bud oil, cobalt amino acid chelate, cobalt carbonate, cobalt proteinate, cod, copper, copper amino acid chelate, copper amino acid complex, copper oxide, copper proteinate, copper sulfate, corn, corn bran, corn flour, corn germ meal, corn gluten, corn gluten meal, corn grits, corn meal, corn oil, corn starch, corn starch-modified, corn syrup, cracked barley, cracked pearled barley, cranberries, cranberry powder, deboned chicken, deboned lamb, deboned turkey, dehydrated alfalfa, dehydrated alfalfa meal, dehydrated carrots, dehydrated potatoes, dextrose, DHA, dicalcium phosphate, DL-alpha tocopherol acetate, DL-methionine, dried animal digest, dried apples, dried *Bacillus licheniformis* fermentation extract, dried *Bacillus subtilis* fermentation extract, dried beet pulp, dried beet pulp (sugar removed), dried blueberries, dried brewers yeast, dried buttermilk, dried capsicum, dried carrots, dried cellulose, dried cheddar cheese, dried cheese, dried cheese powder, dried chicken cartilage, dried chicken liver, dried chicken stock, dried chickory root, dried citrus pulp, dried cooked turkey, dried cranberries, dried egg, dried egg powder, dried egg product, dried eggs, dried garlic, dried ginger, dried grape pomace, dried green beans, dried kelp, dried kelp meal, dried liver digest, dried meat by-product, dried paprika, dried parsley flakes, dried peas, dried plain beet pulp, dried potatoes, dried spinach, dried sweet potato, dried tomato pomace, dried vegetable fiber carrots, dried whey, dried yam, duck, durum flour, durum semolina enriched with thiamine mononitrate, egg noodles, egg pieces, egg product, eggs, *Enterococcus faecium*, ethoxyquin, eucalyptus oil, ferrous sulfate, fiber, fish, fish broth, fish meal, fish meal natural, fish oil, flax meal, flax seed, flaxseed meal, folic acid, folic acid pyridoxine hydrochloride, food starch, fresh, fresh chicken, fresh chicken by-products, fructooligosaccharides, fumaric acid, garlic, garlic extract, garlic flavor, garlic oil, garlic powder, gelatin, ginger, ginger extract, glucosamine, glucosamine hydrochloride, glycerin, glycerine, glyceryl monostearate, glycine, green beans, green tea, ground corn, ground flax seed, ground psyllium seed, ground rice, ground wheat, ground wheat flour, ground whole grain barley, ground whole grain corn, ground whole grain sorghum, ground whole grain wheat, ground whole peas, ground whole wheat, ground yellow corn, guar gum, gum arabic, halibut, herring meal, herring oil, hydrochloric acid, inositol, iodine, iodized salt, iron amino acid chelate, iron amino acid complex, iron oxide, iron proteinate, iron sulfate, L-alanine, L-arginine, L-ascorbyl-2-polyphosphate, L-ascorbyl-2-polyphosphate a, L-carnitine, L-lysine, L-lysine monohydrochloride, L-tryptophan, *Lactobacillus acidophilus*, lamb, lamb broth, lamb by-product, lamb digest, lamb fat, lamb liver, lamb meal, lamb stock, lamb tripe, lecithin, lentils, lettuce, liver, locust bean gum, lutein, lycopene, lysine, mackerel, magnesium oxide, malt extract, malted barley flour, manganous sulfate, manganese amino acid chelate, manganese oxide, manganese proteinate, manganese sulfate, manganous oxide, manganous oxide calcium iodate, manganous proteinate, manganous sulfate, maple syrup, marigold extract, marigold meal, meat and bone meal natural, meat and liver meal, meat by-products, menadione dimethylpyrimidinol bisulfite, menadione sodium bisulfite complex, menadione vitamin K3, menhaden fish meal, menhaden fish oil, milk, mixed tocopherols, mixed vegetable fiber carrots, modified food starch, modified starch, molasses, monocalcium phosphate, monosodium phosphate, natural and artificial chicken flavor, natural and artificial flavors, natural chicken flavor, natural color, natural flavor, natural poultry flavor, natural smoke flavor, niacin, niacin & ferrous sulfate, non-fat yogurt, oat bran, oat fiber, oat groats, oat meal, oats, ocean fish, ocean fish meal, ocean whitefish, omega fatty acids, onion extract, onion powder, pantothenate, paprika oleoresin, parsley, parsley flakes, parsley oil, parsley powder, partially hydroge-nated soybean oil, pasta, pea fiber, pea protein, peanut hulls 10.8%, pearled barley, peas, peppers, petrolatum, philloquinone vitamin K1, phosphoric acid, pork broth, pork by-products, pork liver, potassium sorbate, potassium amino acid complex, potassium chloride, potassium citrate, potassium iodide, potassium iodine, potassium sorbate, potato, potato fiber, potato starch, poultry, poultry by-product meal, poultry by-products, poultry fat, poultry giblets, poultry liver, powdered cellulose, powdered cellulose 11.1%, propionic acid, propyl gallate and citric acid, propylene glycol, pyridoxine hydrochloride, psyllium, rabbit, rabbit by-products, rabbit stock, red 3, red 40 and other color, red peppers, riboflavin, rice, rice bran, rice flour, rice gluten, rice hulls, rice protein concentrate, rosemary, rosemary extract, rosemary extract and citric acid, rye, sage, salmon, salmon broth, salmon meal, salmon oil, salt, sea salt, selenium, shrimp, smoke flavor, sodium alginate, sodium ascorbate, sodium bisulfate, sodium carbonate, sodium caseinate, sodium chloride, sodium hexametaphosphate, sodium metabisulfate, sodium nitrite for color retention, sodium phosphate, sodium propionate, sodium selenite, sodium silico aluminate, sodium tripolyphosphate, sodium tripolyphosphate, sorbic acid, sorbitol, soy flour, soy hulls, soy lecithin, soy protein concentrate, soy protein isolate, soya oil, soybean hulls, soybean meal, soybean mill run, soybean oil, spearmint, spinach, spirulina, starch, steamed bone meal, sucrose, sufficient water for processing, sugar, sun-cured alfalfa meal, sunflower meal, sunflower oil, sweet potato powder, sweet potatoes, tallow, tapioca starch, taurine, tetra sodium pyrophosphate, textured vegetable protein, thiamine, thiamine hydrochloride, thiamine mononitrate, thyme, titanium dioxide, titanium dioxide color, tomato flakes, tomato paste, tomato pomace, tomatoes, trace minerals (calcium sulfate), trace minerals (copper sulfate), trace minerals (potassium chloride), trace minerals (sodium tripolyphoshate), trace minerals (zinc oxide), trace minerals (zinc proteinate), trace minerals (zinc sulfate), tricalcium phosphate, tuna, tuna meal, turkey, turkey broth, turkey by-product meal, turkey natural, turkey stock, turmeric, veal, veal broth, vegetable oil, venison, venison by-products, venison liver, venison meal, venison meat, venison stock, vitamin A, vitamin A & D3, vitamin A acetate, vitamin B1, vitamin B12, vitamin B12 and D3, vitamin B2, vitamin B6, vitamin C, vitamin D3, vitamin D3 and E, vitamin E, vitamin K, water, water cress, water sufficient for processing, watercress and spinach, wheat, wheat bran, wheat flour, wheat germ meal, wheat gluten, wheat middlings, wheat mill run, wheat starch, whey, white fish, whitefish, whitefish meal, whole brown rice, whole carrots, whole cranberries, whole eggs, whole garlic cloves, whole grain corn, whole grain wheat, whole ground barley, whole ground brown rice, whole ground oats, whole ground wheat, whole rice, whole sweet potatoes, whole wheat, whole wheat flour, wild rice, xanthan gum, yeast culture, yellow 5, yellow 6, yellow squash, yellow zucchini, yucca schidigera, yucca schidigera extract, zinc amino acid chelate, zinc amino acid complex, zinc oxide, zinc proteinate, zinc proteinate and zinc sulfate.

Most preferred ingredients are: alpha-lipoic acid, preferably in an amount sufficient to promote formation of healthy skin and/or coat; for antibiotic purposes preferred ingredients are alpha-lipoic acid, dried garlic, garlic extract, garlic oil and garlic powder; lecithin, preferably as an antioxidans; cracked barley, cracked pearled barley, ground whole grain corn, ground whole grain sorghum, herring oil, mackerel, menhaden fish oil, ocean fish, whole brown rice and whole sweet potatoes are preferred as sources of energy; preferred sources of fiber are dehydrated carrots, dried apples, ground whole grain barley, oat bran, oat groats, oat meal, whole ground barley, whole ground oats; cobalt proteinate (source of chelated cobalt), copper proteinate, iron proteinate, manganese proteinate, manganous proteinate, trace minerals and, zinc proteinate are preferred sources of minerals; preferred sources of omega-3 fatty acids are borage oil, canola oil, canola oil (preserved with mixed tocopherols) and flax seed; rosemary extract and citric acid are preferred preservatives; preferred sources of protein are beef meal, chicken meal, dried peas, halibut, lamb meal, menhaden fish meal, ocean whitefish, peas, venison meal, whole ground brown rice and whole ground wheat; preferred sources of vitamins are calcium ascorbate, carrots, dried carrots, mixed tocopherols, whole carrots; preferred replacements for plain water, and also preferred flavours, are beef broth, chicken broth, lamb broth, lamb stock and turkey broth.

Ingredients not most but also highly preferred are: alfalfa concentrate powder, alfalfa dehydrated meal, chicken fat, chicken liver, fresh, ocean fish meal and pearled barley as sources of energy; green beans, ground whole peas, oats and pea fiber as sources of fiber; cobalt amino acid chelate, copper amino acid chelate, copper amino acid complex, dried kelp meal, iron amino acid chelate, manganese amino acid chelate, manganese sulfate, potassium amino acid complex, zinc amino acid chelate as sources of minerals; chicory extract, ginger extract and yucca schidigera extract as prebiotics; good preservatives are garlic, rosemary and sage; alfalfa nutrient concentrate, catfish, catfish meal, cod, duck, eggs, ground whole wheat, herring meal, pea protein, rabbit, shrimp, tuna, venison, venison meat, white fish, whitefish, whitefish meal, whole wheat, are preferred as sources of protein; beta carotene and folic acid are preferred sources of vitamins; chicken stock, rabbit stock, turkey stock, veal broth and venison stock are preferred replacements for plain water, and also preferred flavours.

A standard food of feed composition of the present invention, preferably a pet food, preferably comprises one or more ingredients of the group consisting of vitamin B-12, biotin, calcium carbonate, calcium pantothenate, choline chloride, cobalt carbonate, copper sulfate, vitamin D3 and E supplements, DL-methionine, dried kelp, ferrous sulfate, folic acid, inositol, manganese oxide, manganous oxide, manganous sulfate, menadione sodium bisulfite complex, mineral supplements including zinc sulfate, natural flavor, niacin and ferrous sulfate, niacin supplement, potassium chloride, potassium iodide, pyridoxine hydrochloride, riboflavin, sodium selenite, taurine, thiamine, thiamine mononitrate, thiamine mononitrate, vitamin A, vitamin A & D3, vitamin A acetate, vitamin B12, vitamin D3, water, zinc oxide and zinc sulfate.

The feed as used in accordance with the present invention maybe any feed comprising the binder microorganism or fragment thereof as an active ingredient. The feed includes, for example, pet feeds for dogs, cats and rats, and cattle feeds for cows and pigs.

The feed can be produced by appropriately blending the active ingredient as described herein above in a raw feed material including, for example, cereals, brans, oil-seed meals, animal-derived raw feed materials, other raw feed materials and purified products as indicated above. Preferred feeds of the present invention are chew products. Preferred products are pig ears, bull sinews, cattle tails, oesophagus, dried muscle meat, pig feet and dried pressed cowhide, buffalo hide or composite chew products, containing plant materials as e.g. fibers, brans etc. Other chew products are known in the art and are also preferred, for example the chew products of U.S. Pat. No. 2,988,045, WO 01/50882 A2, EP 1 151 674 A1, EP 1 006 789 A1 and CH 676200 A5. The chew product preferably is in the shape of a bone, a roll, a donut, a bow, a pretzel, a figure eight, or a chip.

In case of providing to animals the feed according to the present invention, the amount of the feed to be ingested is not specifically limited but is preferably, for example, 0.1 mg to 50 g per 1 kg body weight per day, preferably 0.5 mg to 20 g per 1 kg body weight per day, based on the amount of the active ingredient. The feed is continuously ingested at this amount for a period from a single day up to 5 years, preferably from 2 weeks to one year. Again, the amount ingested can be adjusted to an appropriate range depending on the species, age and body weight of the animal ingesting the feed, and the like.

It is likewise preferred that the composition of the present invention comprises one or more probiotic microorganisms or products obtained thereof, independently of the binder microorganism and fragment thereof. Preferred probiotic microorganisms and respective products thereof are *Bacillus subtilis*, *Bifidobacterium longum*, *Bifidobacterium pseudolongum*, *Bifidobacterium thermophilum*, dried *Bacillus licheniformis* fermentation extract, dried *Bacillus subtilis* fermentation extract, *Enterococcus faecium* and *lactobacillus acidophilus*.

Particularly preferred are food and feed compositions further comprising, in addition to the binder microorganism or fragment thereof, a further microorganism for preventing and/or treating oral malodor. Most preferred are food and feed compositions further comprising such microorganism as disclosed in WO 2009/149816 A1, which is incorporated herein in its entirety, Of these, the further microorganism is preferably selected from the group consisting of *Lactobacillus acidophilus* having DSMZ accession number DSMZ 19825, DSMZ 19826, DSMZ 19827.

The invention is now further described by selected examples and embodiments. These embodiments and examples are intended to represent certain preferred features of the present invention, without limiting the scope of this description or the scope of the claims. It is to be understood that the skilled artisan can devise further working examples and embodiments by his common general knowledge and the instructions and explanations given in this description and the documents incorporated herein by reference.

Example 1: Storage and Growth of Binder Microorganisms

Storage and growth of strains can be performed according to ordinary procedures. According to this present example, strains are stored as frozen stocks at −80° C. 1 ml of a culture is grown to stationary phase (OD600: 4-8) in MRS-Medium and mixed with 500 µl of a sterile 50% glycerine solution and frozen. Cultures of *mutans Streptococci* are grown in TSY-media to stationary phase (OD600 1-2) and are treated as mentioned above for frozen storage.

Cultivation of *mutans Streptococci* (*S. mutans*, *S. sobrinus*, *S. ratti*, *S. cricetus*, *S. ferus* or *S. macacae*) as well as cultivation of lactobacilli can be done in 5 ml in closed Falcon tubes at 37° C. without shacking over night.

In particular, the strains used in the present application were stored as frozen stocks at −80° C. 1 ml of a culture grown to stationary phase (OD600/ml_4-8) in MRS-broth was mixed with 500 µl of a sterile 50% glycerol solution and frozen.

In particular, cultures of *mutans Streptococci* were grown in TSY-broth to stationary phase (OD600/ml_1-2) and treated as mentioned above.

Cultivation of *mutans Streptococci* (*S. mutans* (DSMZ 20523, serotype c; NCTC 10923, serotype e; NCTC 11060, serotype f), *S. sobrinus* DSMZ 20742, *S. ratti* DSMZ 20564, *S. cricetus* DSMZ 20562, *S. ferus* DSMZ 20646 or *S. macacae* DSMZ 20714) and cultivation of lactobacilli was done in 5 ml in closed Falcon tubes at 37° C. without shacking over night. For the fluorescence assays as described in Example 5 *S. mutans* DSMZ 20523 was used.

For an aggregation assay the lactobacilli were grown in MRS-medium. 5 ml MRS-medium were inoculated with 10 µl of the stock and incubated for 3 days at 37° C. under aerobic conditions. The optical density of the culture at 600 nm (OD600) was measured. The culture was then diluted to an OD600 of 2 using PBS-buffer. The *mutans Streptococci* were grown in 7 ml TSY-medium. 7 ml of TSY-medium were inoculated with 10 µl of the stock and incubated at 37° C. under anaerobic conditions.

MRS-broth:
MRS-mixture (Difco, USA) 55 g/l, pH: 6.5
TSY-broth:
TSY-mixture (Difco, USA) 30 g/l
Yeast extract (Deutsche Hefewerke, Germany) 3 g/l
Buffer:
PBS-buffer:
$Na_2HPO_4$ $2H_2O$ 1.5 g/l
$KH_2PO_4$ 0.2 g/l
NaCl 8.8 g/l
pH adjusted with HCl

Example 2: Taxonomic Classification of Binder Strains and *Streptococcus* Strains The taxonomic classification of the strains was done according to their carbohydrate fermentation pattern. This was determined using the API 50 CH (bioMerieux, France) system and analyzed using APILAB PLUS software version 3.3.3 (bioMerieux, France).

Example 3: Staining of Cells

After the lactobacilli and the *mutans Streptococci* were grown as described in Example 1, the *mutans Streptococci* were stained using a fluorescence strain. For this, the OD600 of the culture was measured. The culture was harvested by centrifugation at 3200×g for 5 min. the pellet was resuspended in PBS-buffer. The amount of buffer was calculated so that the resulting suspension had an OD600 of 4.2 ml of that suspension were mixed with 2 µl of a CFDA-SE solution (Invitrogen, USA) that was prepared according to the manufacturer's instructions. Staining of the cells was carried out by incubating the mixture for 2 h at 37° C. The stained cells were harvested by centrifugation at 3200×g for 5 min. The cells were subsequently resuspended in 2 ml PBS-buffer.

Example 4: Pelleting Aggregation Assay of *Mutans Streptococci*

For the assay, mixing of lactobacilli and *mutans Streptococci* was done in volumetric ratios of 3:1 to 60:1 (*mutans*

Streptococci:lactobacilli), this corresponds to a ratio of colony forming units from 1:50 to 1:2.5.

An optical density measured at a wavelength of 600 nm in 1 ml means preferably for *mutans Streptococci* $3 \times 10^8$ colony forming units and for lactobacilli preferably $7 \times 10^9$ colony forming units. Mixing was done in 2 ml volume in 15 ml Falcon tubes. The culture suspensions were diluted with PBS-buffer to obtain the volumetric ratios mentioned above while keeping the final volume at 2 ml. The mixture was vortexed for 15 seconds.

An aggregation is visible as an immediate turbidity of the suspension. The tubes were left undisturbed for 20 min, after that period of time the aggregates settle as a visible pellet whereas non-aggregating mixtures stay in suspension. The formed aggregates were separated by centrifugation at 500×g for 30 seconds. Afterwards, the amount of aggregation was quantified by measuring the amount of non-aggregated cells that were left in the supernatant. Correspondingly, 1 ml of the supernatant was carefully removed to measure the optical density. The optical density was measured at 600 nm. The value after subtraction of the respective control experiment without lactobacilli represents the amount of cells that have not been aggregated.

As a control, self-aggregation of the respective *Lactobacillus* strain and the *mutans Streptococcus* strains was always investigated by performing the test with only the *Lactobacillus* or the *mutans Streptococcus* strain added to the tube. An aggregation of *S. mutans* by *Lactobacillus* is shown in FIGS. 1 (left tube) and 2.

The lactobacilli strains as described herein above, in particular those deposited with the DSMZ, exhibited aggregation of all *S. mutans* serotypes without showing a self-aggregation behaviour.

Example 5: Fluorescence Aggregation Assay of Mutans Streptococci

Figure 3:
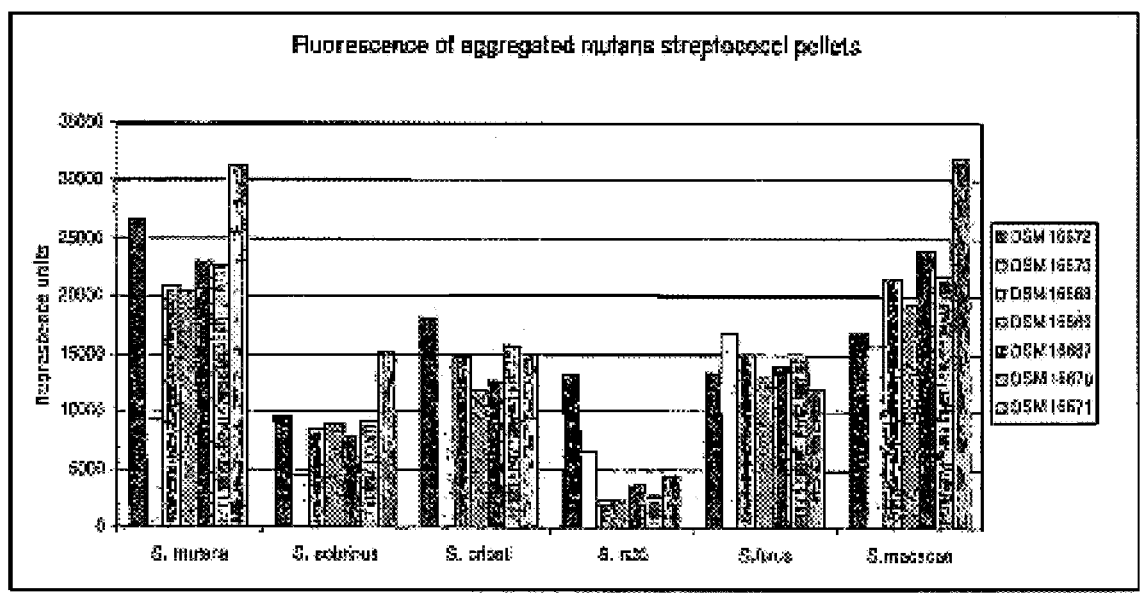
FIG. 3 shows aggregation of *mutans Streptococci* by all tested lactobacilli, as noted in Example 5 below.

For the assay, suspension of the respective *lactobacillus* and the respective stained *mutans Streptococcus* (*S. mutans* DSMZ 20523 with Lb-OB-K1 (DSMZ 16667), *S. mutans* DSMZ 20523 with Lb-OB-K2 (DSMZ 16668), *S. mutans* DSMZ 20523 with Lb-OB-K3 (DSMZ 16669), *S. mutans* DSMZ 20523 with Lb-OB-K4 (DSMZ 16670), *S. mutans* DSMZ 20523 with Lb-OB-K5 (DSMZ 16671), *S. mutans* DSMZ 20523 with Lb-OB-K6 (DSMZ 16672), *S. mutans* DSMZ 20523 with Lb-OB-K7 (DSMZ 16673); *S. sobrinus* DSMZ 20742 with Lb-OB-KI (DSMZ 16667), *S. sobrinus* DSMZ 20742 with Lb-OB-K2 (DSMZ 16668), *S. sobrinus* DSMZ 20742 with Lb-OB-K3 (DSMZ 16669), *S. sobrinus* DSMZ 20742 with Lb-OB-K4 (DSMZ 16670), *S. sobrinus* DSMZ 20742 with Lb-OB-K5 (DSMZ 16671), *S. sobrinus* DSMZ 20742 with Lb-OB-K6 (DSMZ 16672), *S. sobrinus* DSMZ 20742 with Lb-OB-K7 (DSMZ 16673); *S. cricetus* DSMZ 20562 with Lb-OB-KI (DSMZ 16667), *S. cricetus* DSMZ 20562 with Lb-OB-K2 (DSMZ 16668), *S. cricetus* DSMZ 20562 with Lb-OB-K3 (DSMZ 16669), *S. cricetus* DSMZ 20562 with Lb-OB-K4 (DSMZ 16670), *S. cricetus* DSMZ 20562 with Lb-OB-K5 (DSMZ 16671), *S. cricetus* DSMZ 20562 with Lb-OB-K6 (DSMZ 16672), *S. cricetus* DSMZ 20562 with Lb-OB-K7 (DSMZ 16673); *S. ratti* DSMZ 20564 with Lb-OB-K1 (DSMZ 16667), *S. ratti* DSMZ 20564 with Lb-OB-K2 (DSMZ 16668), *S. ratti* DSMZ 20564 with Lb-OB-K3 (DSMZ 16669), *S. ratti* DSMZ 20564 with Lb-OB-K4 (DSMZ 16670), *S. ratti* DSMZ 20564 with Lb-OB-K5 (DSMZ 16671), *S. ratti* DSMZ 20564 with Lb-OB-K6 (DSMZ 16672), *S. ratti* DSMZ 20564 with Lb-OB-K7 (DSMZ 16673); *S. ferus* DSMZ 20646 with Lb-OB-K1 (DSMZ 16667), *S. ferus* DSMZ 20646 with Lb-OB-K2 (DSMZ 16668), *S. ferus* DSMZ 20646 with Lb-OB-K3 (DSMZ 16669), *S. ferus* DSMZ 20646 with Lb-OB-K4 (DSMZ 16670), *S. ferus* DSMZ 20646 with Lb-OB-K5 (DSMZ 16671), *S. ferus* DSMZ 20646 with Lb-OB-K6 (DSMZ 16672), *S. ferus* DSMZ 20646 with Lb-OB-K7 (DSMZ 16673); *S. macacae* DSMZ 20724 with Lb-OB-K1 (DSMZ 16667), *S. macacae* DSMZ 20724 with Lb-OB-K2 (DSMZ 16668), *S. macacae* DSMZ 20724 with Lb-OB-K3 (DSMZ 16669), *S. macacae* DSMZ 20724 with Lb-OB-K4 (DSMZ 16670), *S. macacae* DSMZ 20724 with Lb-OB-K5 (DSMZ 16671), *S. macacae* DSMZ 20724 with Lb-OB-K6 (DSMZ 16672) and *S. macacae* DSMZ 20724 with Lb-OB-K7 (DSMZ 16673)) were mixed. 50 µl of the *lactobacillus* suspension were added to 50 µl of stained *mutans Streptococci* in a 96 well microtiter plate. The plate was vortexed at full speed for 12 minutes. Afterwards the plate was centrifuged at 500×g for 10 seconds. The supernatant was carefully removed and discarded. The pellet was resuspended in 100 µl of PBS-buffer The fluorescence of the suspension was measured in a microtiterplate fluorescence reader at a wavelength of 495 nm for excitation and 525 nm for emission. As controls lactobacilli alone as well as stained *mutans Streptococci* were treated and measured as described. The background fluorescence measured for the respective *mutans Streptococci* alone was subtracted from the value measured for the aggregation with the respective *lactobacillus*. All measurements were done in triplicate. The *mutans Streptococci* were aggregated by all tested lactobacilli (see FIG. 3).

Example 6: Specificity of the Aggregation Towards Typical Members of the Oral Flora The *Lactobacillus* cultures were grown as described in Example 1. The oral bacteria—namely: *Streptococcus salivarius* subsp. *thermophilus* (isolated by OrganoBalance, identified by API 50 CH (Biomerieux, France) according to manufacturer's instructions); *Streptococcus oralis* (DSMZ 20066); *Streptococcus oralis* (DSMZ 20395); *Streptococcus oralis* (DSMZ 20627); *Staphylococcus epidermidis* (DSMZ 1798); *Staphylococcus epidermidis* (DSMZ 20044); *Streptococcus mitis* (DSMZ 12643); *Streptococcus sanguinis* (DSMZ 20567)—were grown in 5 ml BHI-medium in closed 15 ml Falcon tubes at 37° C. over night. Each of the above mentioned oral bacteria was preferably mixed in a volumetric ratio of 3:1 with *Lactobacillus* cultures and aggregation was assayed as in Example 4. For each testing of aggregation/non-aggregation only one of the aforementioned bacteria is preferably used to immediately determine the outcome of the testing.

As a control, a self-aggregation of the respective oral bacteria as well as the tested *Lactobacillus* strains was always investigated by performing the test with only the lactobacilli or the oral flora strains added to the tube.

The *L. paracasei* ssp. *paracasei* strains Lb-OB-KI (DSMZ 16667), Lb-OB-K2 (DSMZ 16668), Lb-OB-K3 (DSMZ 16669), Lb-OB-K4 (DSMZ 16670), Lb-OB-K5 (DSMZ 16671), did not aggregate the oral bacteria mentioned above. They are thus "specifically binding to *mutans Streptococci*" according to the above definition. The *L. rhamnosus* strains Lb-OB-K6 (DSMZ 16672) and Lb-OB-K7 (DSMZ 16673) aggregated *Streptococcus salivarius* subsp *thermophilus*. They are nevertheless considered "specifically binding to *mutans Streptococci*" according to the above less preferred definition.

BHI-broth:
BHI-mixture (Difco, USA) 37 g/L pH: 7.2

Example 7: Temperature Resistance of the Aggregating Capacity of the Lactobacilli The bacteria were grown as in Example 1. The grown lactobacilli cultures were autoclaved at 121° C. at 2 bar in saturated steam for 20 min. After cooling of the autoclaved cultures to room temperature, the lactobacilli were mixed in a volumetric ratio of 1:3 with grown *S. mutans* cultures and aggregation was assayed as in Example 4 including the control experiments. Aggregation was also assayed using the oral bacteria as outlined in Example 6.

It was found that the aggregation behaviour of the lactobacilli was not changed by the autoclaving procedure towards the tested *S. mutans* serotypes or towards the oral bacteria.

Example 8: Aggregation by Heat-Inactivated Lactobacilli

The lactobacilli were grown as described in Example 1. *Mutans Streptococci* were grown and stained as described in Examples 1 and 3. The grown lactobacilli cultures were adjusted to an OD600 of 2 as described in Example 1. 1 ml of that suspension was autoclaved at 121° C. at 2 bar for 20 min as described above. After cooling of the autoclaved cultures to room temperature, aggregation was measured as described in Example 5 including control experiments. The heat-inactivated lactobacilli still aggregated all *mutans Streptococci*.

Example 9: Dependency of the Aggregation on pH-Value

The bacteria were grown as in Example 1. 0.5 ml of the lactobacilli and 1.5 ml of *S. mutans* were harvested by centrifugation at 3200×g for 10 min and the supernatant was discarded. The cells were resuspended in their original volume (0.5 ml and 1.5 ml, respectively) in different PBS-buffers adjusted to different pH-values. The pH-values of the buffers were adjusted to values from 7.0 to 3.0 in steps of 0.5 pH-units. Cultures were resuspended in buffers of the respective pH-value that was to be used for the aggregation behaviour assay.

Afterwards the lactobacilli were mixed in a volumetric ratio of 1:3 with *S. mutans* cultures and aggregation was assayed as in Example 4 including the control experiments. No visible aggregation of *S. mutans* by the lactobacilli occurred at pH values lower than 4.5.

Example 10: Dependency of the Aggregation on pH-Value

The lactobacilli were grown as described in Example 1. *Mutans Streptococci* were grown and stained as described in Examples 1 and 3. Afterwards the aggregation was assayed in different pH-values. For this purpose lactobacilli as well as *streptococci* were resuspended in acetate buffer adjusted to the respective pH. pH values tested were 4.0, 4.5 and 5.0. The aggregation was assayed as described in Example 5. No aggregation of *mutans Streptococci* occurred at pH values lower than 4.5.

Example 11: Sensitivity of the Aggregation Behaviour to Lyophilisation

The bacteria were grown as in Example 1. Aliquots of 1 ml of the lactobacilli cultures were harvested by centrifugation at 3200×g for 10 minutes. The supernatant was discarded and the pellets were lyophilised at room temperature under vacuum for two hours. Resulting dry pellets of each tested *Lactobacillus* strain were stored at room temperature and at 4° C., respectively, for 1 day, 1 week, 2 weeks, 3 weeks and 4 weeks. After the storage time, lyophilised pellets were resuspended in 1 ml PBS-buffer, pH 7.0. The resuspended lactobacilli were mixed in a volumetric ratio of 1:3 with freshly grown *S. mutans* cultures and aggregation was assayed as in Example 4 including the control experiments.

The aggregation behaviour of the mentioned lactobacilli towards *S. mutans* was not changed by the lyophilization or the storage procedures

Example 12: Sensitivity of the Aggregation Behaviour to Lyophilisation

The lactobacilli were grown as described in Example 1. *Mutans Streptococci* were grown and stained as described in Examples 1 and 3. The grown lactobacilli cultures were adjusted to an OD600 of 2 as described in Example 1. 1 ml of that suspension was lyophilized at room temperature under vacuum for two hours. Afterwards, the lyophilised pellets were resuspended in 1 ml PBS-buffer. Aggregation was measured as described in Example 5, including control experiments.

The aggregation behaviour of the mentioned lactobacilli towards *mutans Streptococci* was not changed by the lyophilization.

Example 13: Test on Protease Resistance

The bacteria were grown as in Example 1. Proteases used were Pronase E, Proteinase K, Trypsin, Chymotrypsin (all obtained from Sigma, Germany). Aliquots of 1 ml of the lactobacilli were washed in PBS-buffer by harvesting the cells by centrifugation at 3200×g for 10 minutes and resuspending the pellet in 1 ml PBS-buffer (pH 7.0). Afterwards the cells were harvested again as described above and resuspended in PBS-buffer (pH 7.0) containing the respective protease at a final concentration of 2.5 mg/ml. The suspension was incubated for 1 hour at 37° C. Afterwards the cells were washed and resuspended in PBS-buffer (pH 7.0) as described above.

The aggregation was assayed as in Example 3 including the control experiments. The aggregation behaviour of the mentioned lactobacilli towards *S. mutans* was not changed by treatment with any of the mentioned proteases.

Example 14: Protease Susceptibility of Aggregation Behaviour of the Lactobacilli The lactobacilli were grown as described in Example 1. *Mutans Streptococci* were grown and stained as described in Examples 1 and 3. Used proteases were Pronase E, Proteinase K, Trypsin, Chymotrypsin (all obtained from Sigma, Germany). Aliquots of 1 ml of the lactobacilli were washed in PBS-buffer by harvesting the cells by centrifugation at 3200×g for 10 min and resuspending the pellet in 1 ml PBS-buffer (pH 7.0). Afterwards, the cells were harvested again as described above and resuspended in PBS-buffer (pH 7.0) containing the respective protease at a final concentration of 2.5 mgl/ml. The suspension was incubated for 1 hour at 37° C. Afterwards, the cells were washed and resuspended in PBS-buffer (pH 7.0) as described above. The aggregation was assayed as described in Example 5 including control experiments. The aggregation behaviour of the lactobacilli towards *mutans Streptococci* was not changed by the treatment with any of the mentioned proteases.

Example 15: Ion Dependency of the Aggregation Behaviour

The bacteria were grown as in Example 1. Aliquots of 1 ml of the lactobacilli were washed in 1 ml 200 mM EDTA solution twice as described above. Afterwards the cells were harvested and resuspended in 1 ml PBS-buffer (pH 7.0).

The aggregation was assayed as in Example 4 and a complete loss of the aggregation ability was observed. Resuspension of the lactobacilli in 1 ml of a 2 mM calcium solution after the two times washing in 200 mM EDTA-solution restored the ability to aggregate *S. mutans*. Resuspension of the EDTA washed cells in up to 100 mM magnesium solution did not restore the ability to aggregate *S. mutans*.

Example 16: Ion Dependency of the Aggregation Behaviour

The lactobacilli were grown as described in Example 1. *Mutans Streptococci* were grown and stained as described in Examples 1 and 3. Aliquots of 1 ml of the lactobacilli were washed in 1 ml 200 mM EDTA solution twice as described above. Afterwards the cells were harvested and resuspended in 1 ml PBS-buffer (pH 7.0). The aggregation was assayed as described in Example 5 and a complete loss of the aggregation ability was observed. Resuspension of the lactobacilli in 1 ml of a 2 mM calcium solution after the two times washing in 200 mM EDTA-solution restored the ability to aggregate *S. mutans*. Resuspension of the EDTA washed cells in up to 100 mM magnesium solution did not restore the ability to aggregate *mutans Streptococci*.

Example 17: Test of Aggregation in the Presence of Saliva

The bacteria were grown as in Example 1. 2 ml aliquots of *S. mutans* cultures were harvested as described above and resuspended in 2 ml of saliva. The saliva was provided by two volunteers and used immediately after winning. The aggregation was assayed as in Example 4.

The aggregation behaviour of the mentioned lactobacilli towards *S. mutans* did not change in the presence of saliva.

Example 18: Aggregation of *Mutans Streptococci* in the Presence of Saliva

Fresh saliva was sampled from volunteers. Saliva-flow was induced by chewing of sugar-free chewing gum. Volunteers collected 15 ml saliva with each sampling. The freshly collected saliva was diluted 1:2 with PBS-buffer for the assay procedure. Lactobacilli and *mutans Streptococci* were cultivated as described in Example 1. *Mutans Streptococci* were stained as described in Example 3, except that after the staining procedure the stained cells were resuspended in saliva, instead of PBS-buffer. The aggregation was measured as described in Example 5 including control experiments. The presence of saliva did not inhibit the aggregation.

Isolation Example 1: Obtaining of Further Lactobacilli

Lactobacilli can be obtained from any source, e.g. by oral cavity swabs of volunteers with low amount of caries and/or dental calculus. Also, Lactobacilli can be obtained from cell culture collections like DSMZ and ATCC, or from other known sources of lactic acid bacteria, e.g. plants, foods and feeds. Strains obtained are then purified by standard microbiological techniques. Selective media for Lactobacilli are for example described by Rogosa et al. 1951. A selective medium for the isolation of oral and fecal lactobacilli, J. Bacteriol. 62: 132-133.

Isolated strains are grown as described in Example 1. Selection for binding is performed as described in Isolation Example 2.

Isolation Example 2:

Stained *Streptococcus mutans* (DSMZ 20523) was prepared and distributed to 96 well microtiter plates as described above in Example 5. Also as described in Example 5, 50 µl of the strains to be screened for binding grown according to example 1 were added to each microtiter plate well and vortexed at full speed for 12 minutes. Afterwards, the plate was centrifuged at 500×g for 10 seconds and supernatant was carefully removed. The pellet was resuspended in 100 µl PBS and fluorescence of the suspension was measured as described in Example 5.

The strains to be screened were then tested as described above in Example 5 for binding to *S. mutans* DSMZ 20523, *S. sobrinus* DSMZ 20742, *S. cricetus* DSMZ 20562, *S. ratti* DSMZ 20564, *S. ferus* DSMZ 20646 and *S. macacae* DSMZ 20724. Positive binders were found to produce aggregates.

Food and Feed Example 1: Dog Puppy Feed

Main Ingredients: beef, brown rice, canola seed, flax seed meal, sunflower seed, buckwheat seed (soba), barley, millet.

Lesser Ingredients: carrots, red beets, broccoli, high-oleic sunflower oil, canola oil, sea salt, oregano, garlic, a scorbic acid, propolis, vitamins (vitamins A, B12, D3, C, E, thiamine, riboflavin, pyridoxine, biotin, folic acid, pantothenate, niacin), minerals (chrome, sodium selenite, iron, cooper citrate, zinc sulfate, cobalt).

To 1 kg of a base composition having the above main and lesser ingredients, 3 g of dried autoclaved binder microorganisms and fragments thereof were added. The microorganism material was prepared by growing the binder microorganism as described in Example 1. That is, lactobacilli were grown in MRS-medium. 5 ml MRS-medium were inoculated with 10 µl of the stock and incubated for 3 days at 37° C. under aerobic conditions. The microorganisms were pelleted by centrifugation and washed with PBS once. The resuspended microorganisms were autoclaved as described in Example 8. The autoclaved microorganisms were dried in an oven at 75° C. over night to obtain the dried heat-inactivated binder microorganisms and fragments thereof. The dog puppy food was prepared with each of the deposited *Lactobacillus* strains DSMZ 16667, 16668, 16669, 16670, 16671, 16672 and 16673 separately to obtain 7 separate puppy foods.

The total content of the following parts is (in wt.-% of the total feed):
Protein (min) 26.0
Fat (min) 14.0
Fiber (max) 5.0
Moisture (max) 10.5
Adult Dog Feed Main Ingredient: beef, brown rice, canola seed, flax seed meal, sunflower seed, buckwheat seed (soba), barley, millet.

Lesser Ingredients: carrots, red beets, broccoli, high-oleic sunflower oil, canola oil, sea salt, oregano, garlic, ascorbic acid, propolis, vitamins (i.e. vitamins A, B12, D3, C, E, thiamine, riboflavin, pyridoxine, biotin, folic acid, pantothenate, niacin), minerals (chrome, sodium selenite, iron, cooper citrate, zinc sulfate, cobalt).

As described for the dog puppy food, 7 adult dog food preparations were prepared using the deposited *Lactobacillus* strains DSMZ 16667, 16668, 16669, 16670, 16671, 16672 and 16673 separately.

The total content of the following parts is (in wt.-% of the total feed):
Protein (min) 20.0
Fat (min) 12.0
Fiber (max) 5.0
Moisture (max) 10.5
Vegetarian Dog Feed.

Main Ingredients: soymeal, brown rice, canola seed, flax seed meal, sunflower seed, buckwheat seed, barley, millet, Lesser Ingredients: carrots, red beets, broccoli, high-oleic sunflower oil, canola oil, sea salt, oregano, garlic, ascorbic acid, propolis, vitamins (i.e. vitamins A, B12, D3, C, E, thiamine, riboflavin, pyridoxine, biotin, folic acid, pantothenate, niacin), minerals (i.e. chrome, sodium selenite, iron, cooper citrate, zinc sulfate, cobalt).

As described for the dog puppy food, 7 vegetarian dog food preparations were prepared using the deposited *Lactobacillus* strains DSMZ 16667, 16668, 16669, 16670, 16671, 16672 and 16673 separately.

The total content of the following parts is (in wt.-% of the total feed):
Protein (min) 20.0
Fat (min) 12.0
Fiber (max) 9.0
Moisture (max) 10.5.

All food preparations were fed to a separate group of 5 dogs of the appropriate age (1-8 months, 2-4 years and 2-4 years, respectively) once per day. As required by the dogs, other standard feed was provided at other times of the day. However, except for the above food preparations according to the invention no other feed was provided that was advertised by the respective manufacturer as particularly promoting oral health. After 6 months, none of the dogs had developed dental calculus. Also, oral malodor of the dogs measured by 10 volunteers 3 h after last feeding was considered tolerable.

Food and Feed Example 2: Dog Chew Product

A strip of cow rawhide was dunked in a culture of binder microorganism strains DSMZ 16667, 16668, 16669, 16670, 16671, 16672 and 16673, respectively. The binder microorganisms were grown as described in Food and Feed Example 1. The rawhide strips were then formed into a bone-like shape and autoclaved as described in Food and Feed Example 1.

The autoclaved strips were air dried. The dried bone-like strips were given to 5 dogs of 5-8 years which just had their dental calculus removed. New dried bone-like strips were then given twice per week. Except for the dried bone-like strips, the dogs were fed as before removal of dental calculus. Within 8 months, none of the dogs developed dental calculus again. Also, oral malodor of the dogs measured by 10 volunteers 3 h after last feeding was considered tolerable.

Food and Feed Example 3: Further Dog Feeds
Puppy feed:

Main ingredients: chicken, chicken meal, barley, peas, brown rice, ground extruded whole soybeans, chicken fat (preserved with mixed tocopherols).

Lesser ingredients: salmon meal, natural chicken liver flavor, brewers dried yeast, flaxseed meal, dried eggs, apples, carrots, potassium chloride, dicalcium phosphate, minerals (i.e. zinc proteinate, iron proteinate, copper proteinate, manganese proteinate, sodium selenite, cobalt proteinate, calcium iodate), salt, choline chloride, vitamins (i.e. vitamin E supplement, 1-ascorbyl-2-polyphosphate, vitamin B12 supplement, d-calcium pantothenate, vitamin A supplement, niacin, riboflavin, folic acid, biotin, pyridoxine hydrochloride, thiamine mononitrate, vitamin D3 supplement, calcium carbonate), yeast culture (*Saccharomyces cerevisiae*), dried *Enterococcus faecium* fermentation product, dried *Lactobacillus acidophilus* fermentation product, dried *Aspergillus niger* fermentation extract, *trichoderma longibrachiatum* fermentation extract, dried *Bacillus subtilis* fermentation extract and fermentation solubles The total content of the following parts is (in wt.-% of the total feed):
Protein wt.-% (min): 28.0
Fat wt.-% (min): 15.0
Fiber wt.-% (max): 3.5
Moisture wt.-% (max): 10.0.
Adult Dog Feed:

Main ingredients: chicken, chicken meal, barley, peas, oats, brown rice, chicken fat (preserved with mixed tocopherols).

Lesser ingredients: natural chicken liver flavor, brewers dried yeast, salmon meal, dried eggs, apple, whole flaxseed, carrots, dicalcium phosphate, potassium chloride, salt, minerals (i.e. zinc proteinate, iron proteinate, copper proteinate, manganese proteinate, sodium selenite, cobalt proteinate, calcium iodate), choline chloride, vitamins (i.e. vitamin E supplement, 1-ascorbyl-2-polyphosphate, vitamin B12 supplement, d-calcium pantothenate, vitamin A supplement, niacin, riboflavin, folic acid, biotin, pyridoxine hydrochloride, thiamine mononitrate, vitamin D3 supplement), glucosamine hydrochloride, chondroitin sulfate, yeast culture (*Saccharomyces cerevisiae*), dried *Enterococcus faecium* fermentation product, dried *Lactobacillus acidophilus* fermentation product, dried *Aspergillus niger* fermentation extract, dried *Trichoderma longibrachiatum* fermentation extract, dried *Bacillus subtilis* fermentation extract and fermentation solubles.

The total content of the following parts is (in wt.-% of the total feed):
Protein wt.-% (min): 26.0
Fat wt.-% (min): 13.0
Fiber wt.-% (max): 3.5
Moisture wt.-% (max): 10.0.
Weight control dog feed:

Main ingredients: brown rice, chicken meal, barley, oats, peas, chicken, chicken fat (preserved with mixed tocopherols).

Lesser ingredients: natural chicken liver flavor, brewers dried yeast, salmon meal, dried eggs, apple, whole flaxseed, carrots, dicalcium phosphate, potassium chloride, salt, minerals (i.e. zinc proteinate, iron proteinate, copper proteinate, manganese proteinate, sodium selenite, cobalt proteinate, calcium iodate), choline chloride, vitamins (i.e. vitamin E supplement, 1-ascorbyl-2-polyphosphate, vitamin B12 supplement, d-calcium pantothenate, vitamin A supplement, niacin, riboflavin, folic acid, biotin, pyridoxine hydrochloride, thiamine mononitrate, vitamin D3 supplement), glucosamine hydrochloride, chondroitin sulfate, yeast culture (*Saccharomyces cerevisiae*), dried *Enterococcus faecium* fermentation product, dried *Lactobacillus acidophilus* fermentation product, dried *Aspergillus niger* fermentation extract, dried *Trichoderma longibrachiatum* fermentation extract, dried *Bacillus subtilis* fermentation extract and fermentation solubles.

The total content of the following parts is (in wt.-% of the total feed):
Protein wt.-% (min): 24.0
Fat wt.-% (min): 10.0
Fiber wt.-% (max): 3.5
Moisture wt.-% (max): 10.0.

As described for the dog puppy food of Food and Feed Example 1, 7 corresponding puppy, adult and weight control dog food preparations were prepared using the deposited *Lactobacillus* strains DSMZ 16667, 16668, 16669, 16670, 16671, 16672 and 16673 separately.

High protein adult dog feed:

Main Ingredients: De-boned chicken, chicken meal, turkey meal, russet potato, lake whitefish, chicken fat (preserved with mixed tocopherols).

Lesser Ingredients: Sweet potato, whole eggs, turkey, salmon meal, salmon and anchovy oils, salmon, natural chicken flavor, sunflower oil, sun-cured alfalfa, dried brown kelp, carrots, spinach, peas, tomatoes, apples, psyllium, dulse, chicory root, licorice root, tumeric root, fenugreek, glucosamine HCl, cranberries, black currants, marigold flowers, L-carnitine, sweet fennel, *Zea mays*, peppermint leaf, chamomile flowers, dandelion, summer savory, rosemary extract, chondroitin sulfate, rosehips, vitamins (i.e. vitamin E, choline chloride, vitamin A, vitamin D3, thiamine mononitrate, vitamin B12, folic acid, biotin), sea salt, minerals (i.e. iron proteinate, zinc proteinate, manganese proteinate, copper proteinate), dried *Lactobacillus acidophilus* fermentation product, dried *Enterococcus faecium* fermentation product.

The total content of the following parts is (in wt.-% of the total feed):
Protein min: 42 wt.-%
Fat min: 16 wt.-%
Fiber max 3 wt.-%
Moisture max: 10 wt.-%
Ash max: 7 wt.-%.

As described for the dog puppy food of Food and Feed Example 1, 7 corresponding dog feed preparations were prepared using the deposited *Lactobacillus* strains DSMZ 16667, 16668, 16669, 16670, 16671, 16672 and 16673 separately.

Vegetarian Dog Feed:

Main Ingredients: brown rice, canola seed, flax seed meal, sunflower seed, buckwheat seed (soba), barley, millet, carrots, red beets, broccoli, high-oleic sunflower oil.

Lesser Ingredients: canola oil, sea salt, oregano, garlic, ascorbic acid, propolis, vitamins (i.e. vitamins A, B12, D3, C, E, K3, thiamine, riboflavin, pyridoxine, biotin, folic acid, pantothenate, niacin), minerals (i.e. chrome, sodium selenite, iron, cooper citrate, zinc sulfate, cobalt).

The total content of the following parts is (in wt.-% of the total feed):
Protein min: 20 wt.-%
Fat min: 12 wt.-%
Fiber max: 9 wt.-%
Moisture max: 10.5 wt.-%.

As described for the dog puppy food of Food and Feed Example 1, 7 corresponding dog feed preparations were prepared using the deposited *Lactobacillus* strains DSMZ 16667, 16668, 16669, 16670, 16671, 16672 and 16673 separately.

Further Embodiments

1. Binder microorganism or fragment thereof, wherein the microorganism or fragment thereof is capable of binding to at least one, preferably at least two and more preferably at least three *Streptococcus* strain of the *mutans Streptococcus* group, and wherein the binding is resistant to heat treatment and/or resistant to protease treatment and/or is calcium dependent and/or is formed within a pH above 4.0 and/or is independent of magnesium and/or formed in the presence of saliva as an oral care agent.

2. Binder microorganism or fragment thereof according to embodiment 1, wherein the binding is resistant to heat treatment at ≥55° C., preferably at ≥65° C., more preferably at 95-121° C. and most preferably at 121° C.

3. Binder microorganism or fragment thereof according to embodiment 1, wherein the binding is resistant to heat treatment for ≥15 min, preferably 15-120 min, preferably 15-30 min and most preferably 20 min.

4. Binder microorganism or fragment thereof according to embodiment 3, wherein the binding is resistant to heat treatment in saturated steam at a pressure of 1-5 bar, preferably 1-3 bar, more preferably 2 bar.

5. Binder microorganism or fragment thereof according to embodiment 1, wherein the binding is resistant to heat treatment in saturated steam at a pressure of 1-5 bar, preferably 1-3 bar, more preferably 2 bar, at a temperature of 95-121° C., more preferably at 121° C., for ≥15 min, preferably 15-120 min, preferably 15-30 min and most preferably 20 min.

6. Binder microorganism or fragment thereof according to embodiment 1, wherein the binding is resistant to heat treatment, wherein the heat treatment is in saturated steam at a pressure of 2 bar at a temperature of 121° C. for 20 min.

7. Binder microorganism or fragment thereof according to embodiment 1, wherein the binding is resistant to protease treatment by pronase E, proteinase K, trypsin and/or chymotrypsin, and preferably is also resistant to protease treatment by elastase, thrombin, aminopeptidase I, carboxypeptidase, dostripain, endoproteinase, papain, cathepsin B, pepsin, gastricsin, chymosin and/or cathepsin D.

8. Binder microorganism or fragment thereof according to embodiment 7, wherein the binding is resistant to protease treatment by pronase E, proteinase K, trypsin and chymotrypsin.

9. Binder microorganism or fragment thereof according to embodiment 7, wherein the binding is resistant to protease treatment by elastase, thrombin, aminopeptidase I, carboxypeptidase, dostripain, endoproteinase, papain, cathepsin B, pepsin, gastricsin, chymosin and cathepsin D.

10. Binder microorganism or fragment thereof according to embodiment 1, wherein the binding is resistant to heat treatment in saturated steam at a pressure of 1-5 bar, preferably 1-3 bar, more preferably 2 bar, at a temperature of 95-121° C., more preferably at 121° C., for 15 min, preferably 15-120 min, preferably 15-30 min and most preferably 20 min; and also is resistant to protease treatment by pronase E, proteinase K, trypsin and/or chymotrypsin, and preferably is also resistant to protease treatment by elastase, thrombin, aminopeptidase I, carboxypeptidase, dostripain, endoproteinase, papain, cathepsin B, pepsin, gastricsin, chymosin and/or cathepsin D.

11. Binder microorganism or fragment thereof according to embodiment 6, wherein the binding is resistant to protease treatment by pronase E, proteinase K, trypsin and/or chymotrypsin, and preferably is also resistant to protease treatment by elastase, thrombin, aminopeptidase I, carboxypeptidase, dostripain, endoproteinase, papain, cathepsin B, pepsin, gastricsin, chymosin and/or cathepsin D.

12. Binder microorganism or fragment thereof according to embodiment 8, wherein the binding is resistant to heat treatment, wherein the heat treatment is in saturated steam at a pressure of 2 bar at a temperature of 121° C. for 20 min.
13. Binder microorganism or fragment thereof according to embodiment 1, wherein the binding is dependent on the presence of Ca2+ ions in a concentration of at least 2 mM, more preferably at least 1 mM, most preferably at least 0.05 mM.
14. Binder microorganism or fragment thereof according to embodiment 1, wherein the binding is dependent on the presence of Ca2+ ions in a concentration of 0.05-500 mM, more preferably 1-100 mM, most preferably 2-30 mM.
15. Binder microorganism or fragment thereof according to embodiment 12 or 13, wherein the binding is resistant to heat treatment, wherein the heat treatment is in saturated steam at a pressure of 2 bar at a temperature of 121° C. for 20 min.
16. Binder microorganism or fragment thereof according to embodiment 12 or 13, wherein the binding is resistant to protease treatment by pronase E, proteinase K, trypsin and/or chymotrypsin, and preferably is also resistant to protease treatment by elastase, thrombin, aminopeptidase I, carboxypeptidase, dostripain, endoproteinase, papain, cathepsin B, pepsin, gastricsin, chymosin and/or cathepsin D.
17. Binder microorganism or fragment thereof according to embodiment 1, wherein the binding is formed at a pH of 4.0-9.0, preferably 4.0-7.0, more preferably 4.2-5.0 and most preferably 4.5.
18. Binder microorganism or fragment thereof according to embodiment 16, wherein the binding is resistant to heat treatment, wherein the heat treatment is in saturated steam at a pressure of 2 bar at a temperature of 121° C. for 20 min.
19. Binder microorganism or fragment thereof according to embodiment 16, wherein the binding is resistant to protease treatment by pronase E, proteinase K, trypsin and/or chymotrypsin, and preferably is also resistant to protease treatment by elastase, thrombin, aminopeptidase I, carboxypeptidase, dostripain, endoproteinase, papain, cathepsin B, pepsin, gastricsin, chymosin and/or cathepsin D.
20. Binder microorganism or fragment thereof according to embodiment 16, wherein the binding is dependent on the presence of Ca2+ ions in a concentration of at least 2 mM, more preferably at least 1 mM, most preferably at least 0.05 mM.
21. Binder microorganism or fragment thereof according to embodiment 1, wherein the binding is independent of the presence of magnesium ions, and preferably is resistant to heat treatment, wherein the heat treatment is in saturated steam at a pressure of 2 bar at a temperature of 121° C. for 20 min.
22. Binder microorganism or fragment thereof according to embodiment 1, wherein the binding is formed in the presence of saliva, and preferably is resistant to heat treatment, wherein the heat treatment is in saturated steam at a pressure of 2 bar at a temperature of 121° C. for 20 min.
23. Binder microorganism or fragment thereof according to embodiment 1, wherein the binding is resistant to heat treatment, resistant to protease treatment, and is formed in the presence of saliva.
24. Binder microorganism or fragment thereof according to any of the previous embodiments, wherein the strain of mutans Streptococcus is selected from the group consisting of *Streptococcus mutans* serotype c (DSMZ 20523), *Streptococcus mutans* serotype e (NCTC 10923), *Streptococcus mutans* serotype f (NCTC 11060), *Streptococcus sobrinus* DSMZ 20742, *Streptococcus ratti* DSMZ 20564, *Streptococcus cricetus* DSMZ 20562, *Streptococcus ferus* DSMZ 20646 and *Streptococcus macacae* DSMZ 20714, and preferably wherein the specific binding of the binder microorganism or fragment thereof can be assayed as follows:
  (a) growing said binder microorganism to stationary phase, or, in case a fragment is to be tested, obtaining such fragment,
  (b) mixing said binder microorganism or fragment with a mutans Streptococcus which has been grown to stationary phase,
  (c) incubating the mixture obtained in step (b) under conditions allowing the formation of aggregates of said microorganism and said *Streptococcus*, and
  (d) detecting aggregates by the occurrence of a pellet.
25. Binder microorganism or fragment thereof according to any of embodiments 1-22, wherein the microorganism or fragment thereof is capable of binding to each of the strains selected from the group consisting of *Streptococcus mutans* serotype c (DSMZ 20523), *Streptococcus mutans* serotype e (NCTC 10923) and *Streptococcus mutans* serotype f (NCTC 11060).
26. Binder microorganism or fragment thereof according to embodiment 1, 2, 3, 4, 5, 6, 7, 8, 9, 10, 11, 12, 13, 14, 15, 16, 17, 18, 19, 20, 21, 22, 23 or 24, wherein the microorganism or fragment thereof is not capable of binding to at least one, preferably at least two and more preferably at least three and even more preferably all microorganisms selected from the group consisting of *Streptococcus salivarius* ssp. *thermophilus, Streptococcus oralis* DSMZ 20066, *Streptococcus oralis* DSMZ 20395, *Streptococcus oralis* DSMZ 20627, *Streptococcus mitis* DSMZ 12643 and *Streptococcus sanguinis* DSMZ 20567.
27. Binder microorganism or fragment thereof according to embodiment 1, 2, 3, 4, 5, 6, 7, 8, 9, 10, 11, 12, 13, 14, 15, 16, 17, 18, 19, 20, 21, 22, 23, 24 or 25, wherein the binder microorganism is of family Lactobacillaceae, preferably of genus *Lactobacillus*, genus *Paralactobacillus*, genus *Pediococcus* or genus *Sharpea*, more preferably of species *Lactobacillus paracasei*, species *Lactobacillus rhamnosus*, species *Lactobacillus casei* or species *Lactobacillus zeae*, and most preferably is any of strains DSMZ 16667, DSMZ 16668, DSMZ 16669, DSMZ 16670, DSMZ 16671, DSMZ 16672 or DSMZ 16673, or a mutant or derivative thereof.
28. Binder microorganism or fragment thereof according to embodiment 26, wherein the microorganism or fragment thereof is capable of binding to each of the strains selected from the group consisting of *Streptococcus mutans* serotype c (DSMZ 20523), *Streptococcus mutans* serotype e (NCTC 10923) and *Streptococcus mutans* serotype f (NCTC 11060) and is not capable of binding to a microorganism selected from the group consisting of *Streptococcus salivarius* ssp. *thermophilus, Streptococcus oralis* DSMZ 20066, *Streptococcus oralis* DSMZ 20395, *Streptococcus oralis* DSMZ 20627, *Streptococcus mitis* DSMZ 12643 and *Streptococcus sanguinis* DSMZ 20567.
29. Binder microorganism or fragment thereof according to embodiment 26 or 27, wherein the microorganism or fragment thereof, after heat treatment in saturated steam at a pressure of 2 bar at a temperature of 121° C. for 20 min, retains the capability to bind to a mutans *Streptococcus* selected from the group consisting of *Streptococ-* cus mutans serotype c (DSMZ 20523), *Streptococcus mutans* serotype e (NCTC 10923), *Streptococcus mutans* serotype f (NCTC 11060), *Streptococcus sobrinus* DSMZ 20742, *Streptococcus ratti* DSMZ 20564, *Streptococcus cricetus* DSMZ 20562, *Streptococcus ferus* DSMZ 20646 and *Streptococcus macacae* DSMZ 20714 in the presence of at least 0.05 mM calcium ions and in the presence of saliva and independent of a treatment by pronase E, proteinase K, trypsin and/or chymotrypsin, wherein under these conditions the heat treated microorganism or fragment thereof is not capable of binding to a microorganism selected from the group consisting of *Streptococcus salivarius* ssp. *thermophilus, Streptococcus oralis* DSMZ 20066, *Streptococcus oralis* DSMZ 20395, *Streptococcus oralis* DSMZ 20627, *Streptococcus mitis* DSMZ 12643 and *Streptococcus sanguinis* DSMZ 20567.

30. Binder microorganism according to any of embodiments 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30, wherein the binder microorganism is in an inactivated form obtainable or obtained by thermal inactivation, lyphilisation or spray drying, wherein thermal inactivation is preferably achieved by
    autoclaving cells of said binder microorganism at a temperature of 121° C. for at least 20 min in the presence of saturated steam at an atmospheric pressure of 2 bar, or
    freezing said cells for at least 1 h at −20° C.

31. Inactivated binder microorganism according to embodiment 29, obtainable or obtained by thermal inactivation at a temperature of 55° C., preferably at a temperature of 65° C., even more preferably at a temperature of 95-121° C. and most preferably at a temperature of 121° C.

32. Inactivated binder microorganism according to embodiment 30, obtainable or obtained by thermal inactivation for 15 min, preferably 15-120 min, preferably 15-30 min and most preferably 20 min.

33. Inactivated binder microorganism according to embodiment 29, 30 or 31, obtainable or obtained by thermal inactivation in saturated steam at a pressure of 1-5 bar, preferably 1-3 bar, more preferably 2 bar, and most preferably by thermal inactivation in saturated steam at a pressure of 2 bar at a temperature of 121° C. for 20 min.

34. Fragment of a binder microorganism according to any of the previous embodiments, wherein the fragment is a lysate or membrane fragment of a binder microorganism.

35. Binder microorganism or fragment thereof according to any of embodiments 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33, as a sensorically neutral oral care agent.

36. Binder microorganism or fragment thereof according to any of embodiments 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33, as an anti-dental calculus agent, sensorically neutral anti-caries agent and/or anti-oral malodor agent.

37. Binder microorganism or fragment thereof according to embodiment 35, as a sensorically neutral anti-dental calculus agent, sensorically neutral anti-caries agent and/or sensorically neutral anti-oral malodor agent.

38. Binder microorganism or fragment thereof according to any of embodiments 34, 35 or 36, wherein the binder microorganism or fragment thereof is an isolated or purified binder microorganism or fragment thereof.

39. Composition comprising a binder microorganism or fragment thereof according to any of embodiments 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or 37 as an oral care agent, preferably as an anti-dental calculus agent, an anti-caries agent and/or an anti-oral malodor agent.

40. Composition comprising a binder microorganism or fragment thereof according to any of embodiments 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or 37 as a sensorically neutral oral care agent, preferably as a sensorically neutral anti-dental calculus agent, a sensorically neutral anti-caries agent and/or a sensorically neutral anti-oral malodor agent.

41. Composition comprising a binder microorganism or fragment thereof according to any of embodiments 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or 37 in an amount
    sufficient for preventing or reducing intensity of oral malodor, and/or
    sufficient for preventing caries or slowing down caries generation and/or
    sufficient for preventing dental calculus formation or slowing down dental calculus formation.

42. Composition comprising a binder microorganism according to any of embodiments 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 34, 35, 36 or 37, in a concentration of
    $10^2$-$10^{13}$ cells/mg, preferably $10^2$-$10^{12}$ cells/mg, even more preferably $10^3$-$10^8$ cells/mg, or
    $10^2$-$10^{13}$ cells/ml, or
    ≥0.01 wt.-% relative to the total composition, preferably 0.01-10 wt.-% and more preferably 0.025-2 wt.-%, or
    ≥0.01 mg dry weight/g total composition, preferably 0.01-100 mg dry weight/g total composition and more preferably 0.025-2 mg dry weight/g total composition.

43. Composition comprising a fragment of a binder microorganism according to any of embodiments 32, 33, 34, 35, 36 or 37, in a concentration of
    ≥0.01 wt.-% relative to the total composition, preferably 0.01-10 wt.-% and more preferably 0.025-2 wt.-%, or
    ≥0.01 mg dry weight/g total composition, preferably 0.01-100 mg dry weight/g total composition and more preferably 0.025-2 mg dry weight/g total composition.

44. Composition according to any of embodiments 38, 39, 40, 41 or 42, comprising a further microorganism in a viable, a thermally inactivated or lyphilized form, wherein the thermally inactivated form is obtainable or obtained by treatment in saturated steam at a pressure of 1-5 bar, preferably 1-3 bar, more preferably 2 bar, and most preferably by thermal inactivation in saturated steam at a pressure of 2 bar at a temperature of 121° C. for 20 min.

45. Composition according to embodiment 43, wherein the further microorganism is an anti-oral malodor microorganism in a concentration sufficient for preventing, modifying or reducing oral malodor, preferably capable of stimulating the growth of *Streptococcus salivarius* but does not stimulate the growth of *Streptococcus mutans* and/or *Porphyromonas gingivalis*.

46. Composition according to embodiment 44, wherein the anti-oral malodor microorganism is of species *Lactobacillus acidophilus*, and preferably is any of the *Lactobacillus* strains DSMZ 19825, DSMZ 19826 or DSMZ 19827.

47. Composition according to any of embodiments 38, 39, 40, 41, 42, 43, 44 or 45,
wherein the composition is for use with a human or animal, and is a toothpaste, dentifrice, tooth powder, topical oral gel, mouth rinse, denture product, mouthspray, lozenge, oral tablet, chewing gum, mouth wash, dental floss, chew product or an additive for food, feed or drinks, or
wherein the composition is in the form of a powder, tablet, film preparation, solution, aerosol, granule, pill, suspension, emulsion, capsule, syrup, liquid, elixir, extract, tincture or fluid extract, sheet-like food, bottled food, canned food, retort food or fluid food or
wherein the composition is a food or drink selected from the group consisting of gum, spray, beverage, candy, infant formula, ice cream, frozen dessert, sweet salad dressing, milk preparation, cheese, quark, yogurt, acidified milk, coffee cream, whipped cream, butter, cheese, processed milk and skimmed milk, meat product—preferably ham, sausage, and hamburger, fish meat, cake product, egg product—preferably seasoned egg rolls and egg curd, confectionery—preferably cookie, jelly, snacks, and chewing gum—, bread, noodles, pickle, smoked product, dried fish, seasoning.
48. Composition according to any of embodiments 38, 39, 40, 41, 42, 43, 44 or 45, wherein the composition is a food or feed composition.
49. Food or feed composition according to embodiment 47, wherein the composition is for an infant or for a pet animal, preferably a dog, cat, rat, mouse, hamster, guinea pig or monkey.
50. Pet food or feed composition according to embodiment 48, wherein the composition is a pet chew product, and preferably is in the shape of a bone, a roll, a donut, a bow, a pretzel, a figure eight, or a chip.
51. Composition according to any of embodiments 38, 39, 40, 41, 42, 43, 44, 45, 46, 47 or 48, wherein the composition is a cosmetic, pharmaceutical or veterinary composition.
52. Pet food or feed composition,
comprising an inactivated binder microorganism in a thermally inactivated or lyphilized form, wherein the inactivated microorganism is capable of binding to a *Streptococcus* strain of the *mutans Streptococcus* group, and wherein the binding is formed in the presence of saliva and is resistant to heat treatment and calcium dependent, wherein the heat treatment is in saturated steam at a pressure of 2 bar at a temperature of 121° C. for 20 min,
and wherein the *mutans Streptococcus* strain is selected from the group consisting of *Streptococcus mutans* serotype c (DSMZ 20523), *Streptococcus mutans* serotype e (NCTC 10923) and *Streptococcus mutans* serotype f (NCTC 11060),
and wherein the inactivated binder microorganism thereof is not capable of binding to a microorganism selected from the group consisting of *Streptococcus salivarius* ssp. *thermophilus, Streptococcus oralis* DSMZ 20066, *Streptococcus oralis* DSMZ 20395, *Streptococcus oralis* DSMZ 20627, *Streptococcus mitis* DSMZ 12643 and *Streptococcus sanguinis* DSMZ 20567,
and wherein the binder microorganism is present in a sensorically neutral amount
sufficient for preventing or reducing intensity of oral malodor, and/or
sufficient for preventing caries or slowing down caries generation and/or
sufficient for preventing dental calculus formation or slowing down dental calculus formation.
53. Pet food composition according to embodiment 51, wherein concentration of inactivated binder microorganism is
$10^2$-$10^{13}$ cells/mg, preferably $10^2$-$10^{12}$ cells/mg, even more preferably $10^3$-$10^8$ cells/mg, or
$10^2$-$10^{13}$ cells/ml, or
≥0.01 wt.-% relative to the total composition, preferably 0.01-10 wt.-% and more preferably 0.025-2 wt.-%, or
≥0.01 mg dry weight/g total composition, preferably 0.01-100 mg dry weight/g total composition and more preferably 0.025-2 mg dry weight/g total composition.
54. Pet food or feed composition, comprising a fragment according to embodiment 33 in a concentration of
≥0.01 wt.-% relative to the total composition, preferably 0.01-10 wt.-% and more preferably 0.025-2 wt.-%, or
≥0.01 mg dry weight/g total composition, preferably 0.01-100 mg dry weight/g total composition and more preferably 0.025-2 mg dry weight/g total composition.
55. Use of a binder microorganism or fragment thereof according to any of embodiments 1-37 as a sensorically neutral oral care agent, preferably as a sensorically neutral anti-dental calculus agent and/or sensorically neutral anti-caries agent and/or sensorically neutral anti-oral malodor agent.
56. Use of a binder microorganism or fragment thereof according to any of embodiments 1-37 in the manufacture of any of
a medicament for prevention or treatment of dental calculus formation,
a medicament for prevention or treatment of caries,
a medicament for prevention or treatment of oral malodor,
wherein the binder microorganism and/or fragment thereof is in a sensorically neutral amount.

The invention claimed is:
1. A method for reducing malodor in a dog, comprising administering a dog feed composition comprising an effective amount of a fragment of a microorganism belonging to the genus *Lactobacillus*, wherein said fragment is a membrane fraction obtained by a membrane preparation, as a sensorically neutral oral care agent to the dog in need thereof, wherein the microorganism is capable of binding to a microorganism of the group of *mutans Streptococci*, wherein the microorganism is in a thermally inactivated or lyophilized form, and wherein the binding is:
(i) resistant to heat treatment, wherein said heat treatment is carried out at a temperature of more than 95° C. for at least 20 minutes; and
(ii) resistant to protease treatment, wherein said protease treatment is treatment with a protease selected from the group consisting of pronase E, proteinase K, trypsin and Chymotrypsin; and
(iii) calcium-dependent; and
(iv) formed within a pH range between 4.5 and 8.5; and
(v) formed in the presence of saliva; and
(vi) independent of magnesium;
and wherein
the fragment is used as a sensorically neutral anti-oral malodor agent, and wherein the composition is administered in an amount effective to reduce oral malodor in said dog;
wherein the microorganism is selected from the group consisting of strains DSMZ 16667, DSMZ 16668, DSMZ 16669, DSMZ 16670, DSMZ 16671, DSMZ 16672 and DSMZ 16673;

wherein the composition contains 3 g of the microorganism per 1 kg of the composition;
wherein the composition comprises beef, brown rice, canola seed, flax seed meal, sunflower seed, buckwheat seed, barley, and millet.

2. A method for reducing malodor in a dog, comprising administering a dog feed composition comprising an effective amount of a fragment of a microorganism belonging to the genus *Lactobacillus*, wherein said fragment is a membrane fraction obtained by a membrane preparation, as a sensorically neutral oral care agent to the dog in need thereof, wherein the microorganism is capable of binding to a microorganism of the group of *mutans Streptococci*, wherein the microorganism is in a thermally inactivated or lyophilized form, and wherein the binding is:
(i) resistant to heat treatment, wherein said heat treatment is carried out at a temperature of more than 95° C. for at least 20 minutes; and
(ii) resistant to protease treatment, wherein said protease treatment is treatment with a protease selected from the group consisting of pronase E, proteinase K, trypsin and Chymotrypsin; and
(iii) calcium-dependent; and
(iv) formed within a pH range between 4.5 and 8.5; and
(v) formed in the presence of saliva; and
(vi) independent of magnesium;
and wherein
the fragment is used as a sensorically neutral anti-oral malodor agent, and wherein the composition is administered in an amount effective to reduce oral malodor in said dog;
wherein the microorganism is selected from the group consisting of strains DSMZ 16667, DSMZ 16668, DSMZ 16669, DSMZ 16670, DSMZ 16671, DSMZ 16672 and DSMZ 16673;
wherein the composition contains 3 g of the microorganism per 1 kg of the composition; wherein the composition comprises soymeal, brown rice, canola seed, flax seed meal, sunflower seed, buckwheat seed, barley, and millet.

3. A method for reducing malodor in a dog, comprising administering a dog feed composition comprising an effective amount of a fragment of a microorganism belonging to the genus *Lactobacillus*, wherein said fragment is a membrane fraction obtained by a membrane preparation, as a sensorically neutral oral care agent to the dog in need thereof, wherein the microorganism is capable of binding to a microorganism of the group of *mutans Streptococci*, wherein the microorganism is in a thermally inactivated or lyophilized form, and wherein the binding is:
(i) resistant to heat treatment, wherein said heat treatment is carried out at a temperature of more than 95° C. for at least 20 minutes; and
(ii) resistant to protease treatment, wherein said protease treatment is treatment with a protease selected from the group consisting of pronase E, proteinase K, trypsin and Chymotrypsin; and
(iii) calcium-dependent; and
(iv) formed within a pH range between 4.5 and 8.5; and
(v) formed in the presence of saliva; and
(vi) independent of magnesium;
and wherein
the fragment is used as a sensorically neutral anti-oral malodor agent, and wherein the composition is administered in an amount effective to reduce oral malodor in said dog;
wherein the microorganism is selected from the group consisting of strains DSMZ 16667, DSMZ 16668, DSMZ 16669, DSMZ 16670, DSMZ 16671, DSMZ 16672 and DSMZ 16673;
wherein the composition contains 3 g of the microorganism per 1 kg of the composition; wherein the composition comprises chicken, chicken meal, barley, peas, brown rice, ground extruded whole soybeans, and chicken fat.

4. The method according to claim 1, wherein the composition has a protein content of 20 to 42% by weight, a fat content of 10 to 16% by weight, and a fiber content of 3 to 9% by weight, in each case based on the weight of the composition.

5. The method according to claim 2, wherein the composition has a protein content of 20 to 42% by weight, a fat content of 10 to 16% by weight, and a fiber content of 3 to 9% by weight, in each case based on the weight of the composition.

6. The method according to claim 3, wherein the composition has a protein content of 20 to 42% by weight, a fat content of 10 to 16% by weight, and a fiber content of 3 to 9% by weight, in each case based on the weight of the composition.

* * * * *